(12) United States Patent
Barker et al.

(10) Patent No.: US 10,485,499 B2
(45) Date of Patent: Nov. 26, 2019

(54) METHOD AND SYSTEMS FOR A COMPACT INTEGRATED MONITOR ARM FOR AN IMAGING SYSTEM

(71) Applicant: General Electric Company, Schenectady, NY (US)

(72) Inventors: David Ellis Barker, Salt Lake City, UT (US); Mingtao Liu, Beijing (CN); Cong Peng, Beijing (CN); Samuel Lee Alder, Stansbury Park, UT (US)

(73) Assignee: General Electric Company, Schenectady, NY (US)

( * ) Notice: Subject to any disclaimer, the term of this patent is extended or adjusted under 35 U.S.C. 154(b) by 175 days.

(21) Appl. No.: 15/489,643

(22) Filed: Apr. 17, 2017

(65) Prior Publication Data
US 2018/0296174 A1 Oct. 18, 2018

(51) Int. Cl.
*A61B 6/00* (2006.01)
*A61B 6/10* (2006.01)

(52) U.S. Cl.
CPC .......... *A61B 6/4441* (2013.01); *A61B 6/4405* (2013.01); *A61B 6/4452* (2013.01); *A61B 6/462* (2013.01); *A61B 6/105* (2013.01)

(58) Field of Classification Search
CPC ..... A61B 6/105; A61B 6/4405; A61B 6/4441; A61B 6/4452; A61B 6/462
See application file for complete search history.

(56) References Cited

U.S. PATENT DOCUMENTS

| | | |
|---|---|---|
| 5,627,873 A | 5/1997 | Hanover et al. |
| 6,256,374 B1 | 7/2001 | Tomasetti et al. |
| RE42,091 E | 2/2011 | Moscovitch et al. |
| 8,931,748 B2 | 1/2015 | Bowman et al. |
| 9,413,961 B2 | 8/2016 | Welsh |
| 2010/0239073 A1 | 9/2010 | Eaves |

(Continued)

FOREIGN PATENT DOCUMENTS

JP 2011-115364 A 6/2011

OTHER PUBLICATIONS

"Compact design. Clinical versatility. OEC Fluorostar* 7900 Digital Mobile C-arm," GE Healthcare Brochure, Available Online at www3.gehealthcare.com.sg/en-GB/Products/Categories/Surgical_Imaging/Pain_Management/OEC_Fulorostar_7900, Jul. 10, 2012, 14 pages.

(Continued)

*Primary Examiner* — Mark R Gaworecki
(74) *Attorney, Agent, or Firm* — McCoy Russell LLP

(57) ABSTRACT

Various methods and systems are provided for an integrated arm of an imaging device. In one example, an imaging system may comprise: a base unit; a C-arm coupled to the base unit and including an x-ray source and detector positioned on opposite ends of a C-shaped portion of the C-arm; and a display monitor attached to the C-arm via an integrated arm, wherein the display monitor is movable between a first position on a first side of the C-arm, to a second position on a second side of the C-arm by traveling over a top of an upper half of the C-shaped portion. In this way, the integrated arm may provide a simplified means of orienting the display monitor while promoting better performance of the imaging system.

19 Claims, 14 Drawing Sheets

(56) References Cited

U.S. PATENT DOCUMENTS

| | | | |
|---|---|---|---|
| 2012/0016222 A1* | 1/2012 | Bouvier | A61B 6/102 600/407 |
| 2014/0192962 A1 | 7/2014 | Eaves | |
| 2015/0049856 A1* | 2/2015 | Ritschl | A61B 6/4078 378/14 |

OTHER PUBLICATIONS

"Ziehm Solo Superb imaging meets versatile design," Ziehm Imaging Brochure, Available Online at www.ziehm.com/us/products/ziehm-solo/, Jun. 2016, 8 pages.

Extended European Search Report and Opinion issued in connection with corresponding EP Application No. 18167506.7 dated Sep. 17, 2018, 7 pages.

* cited by examiner

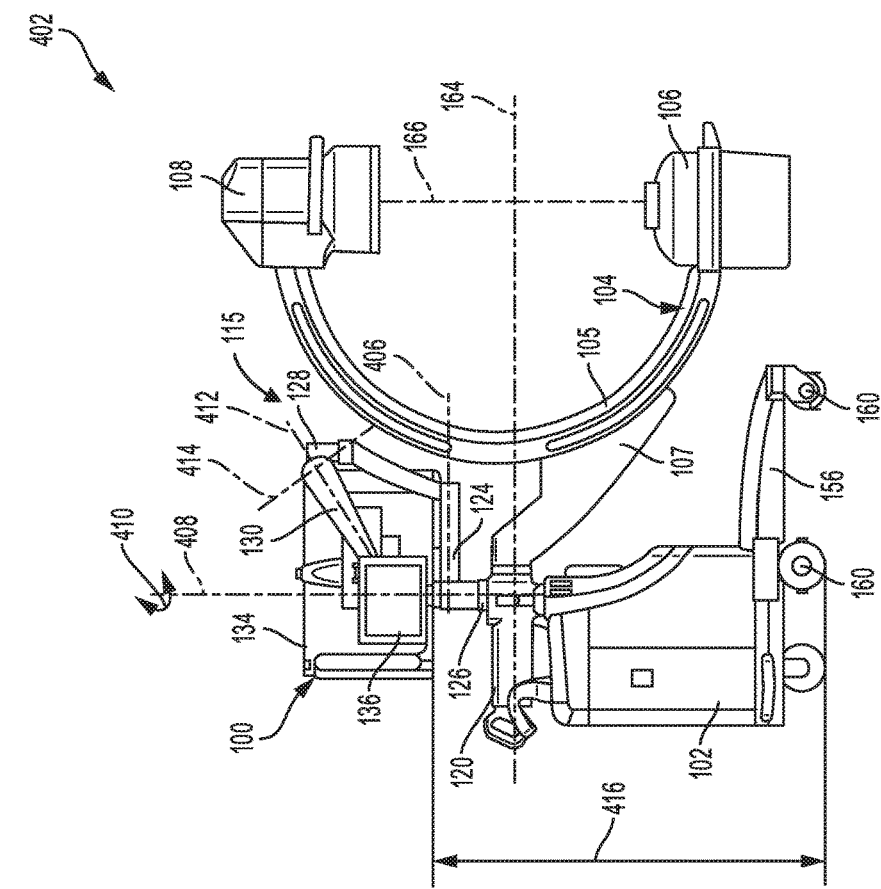
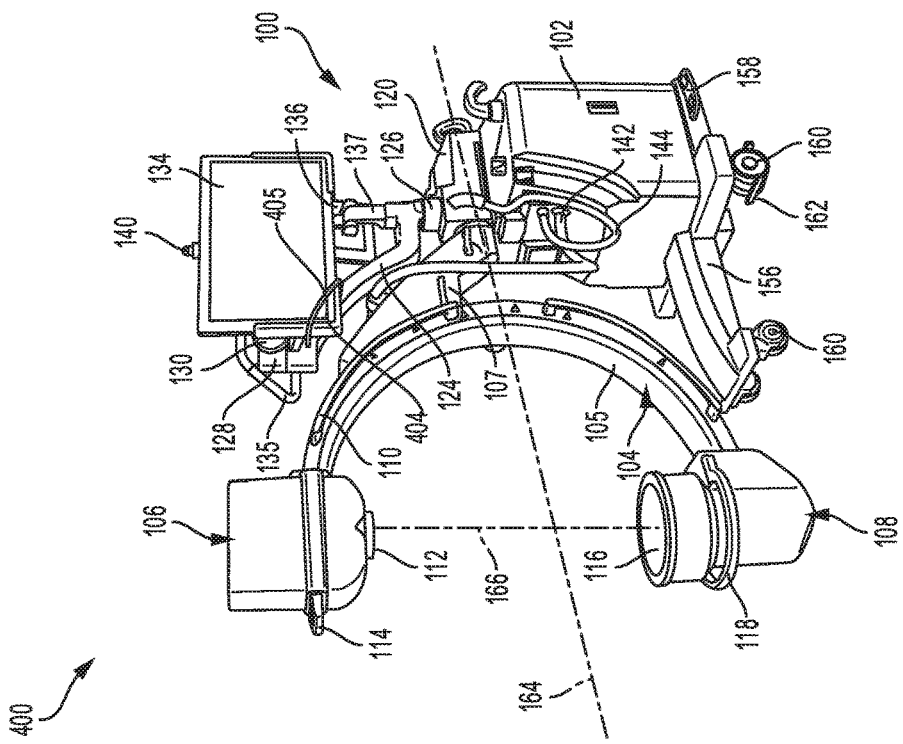

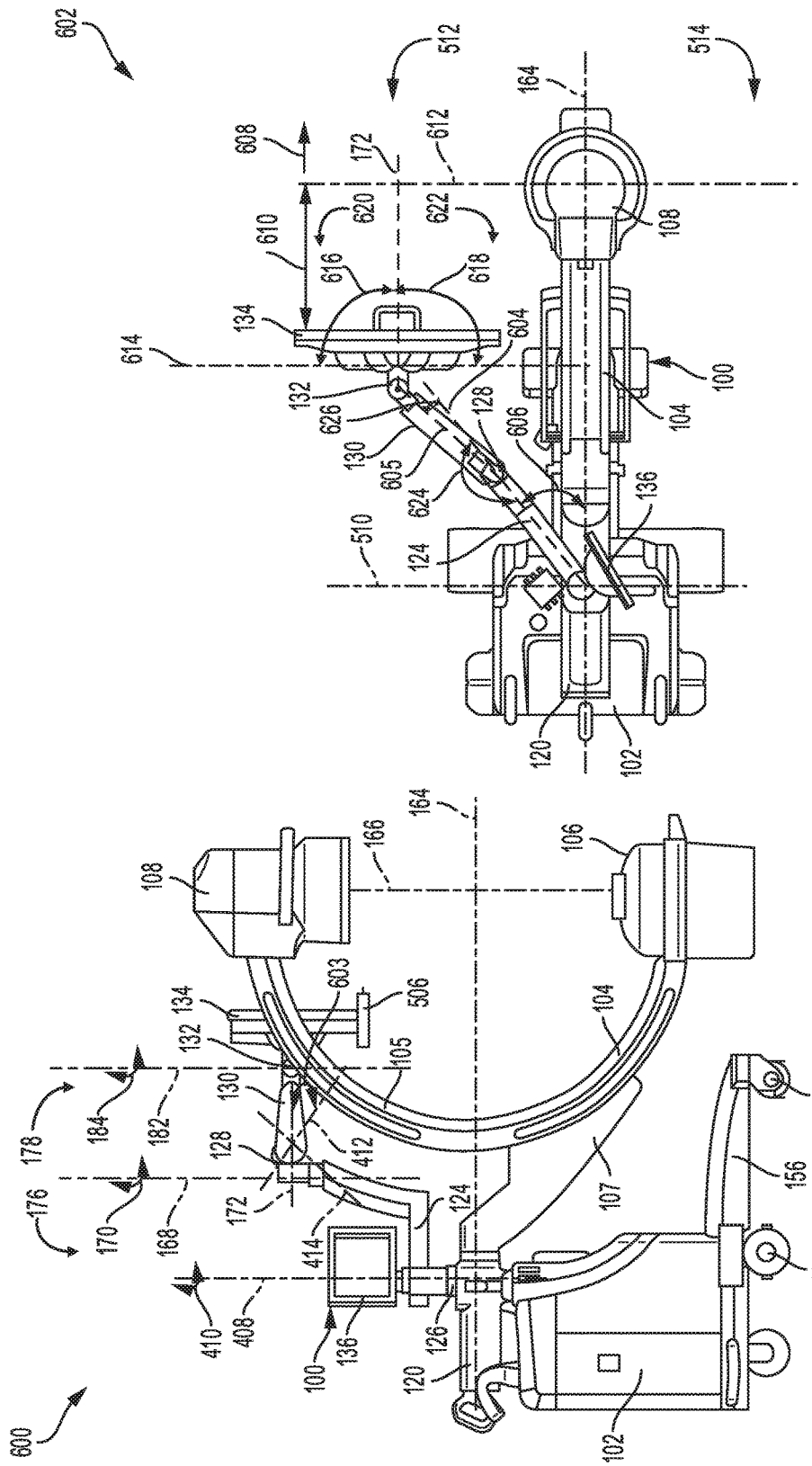

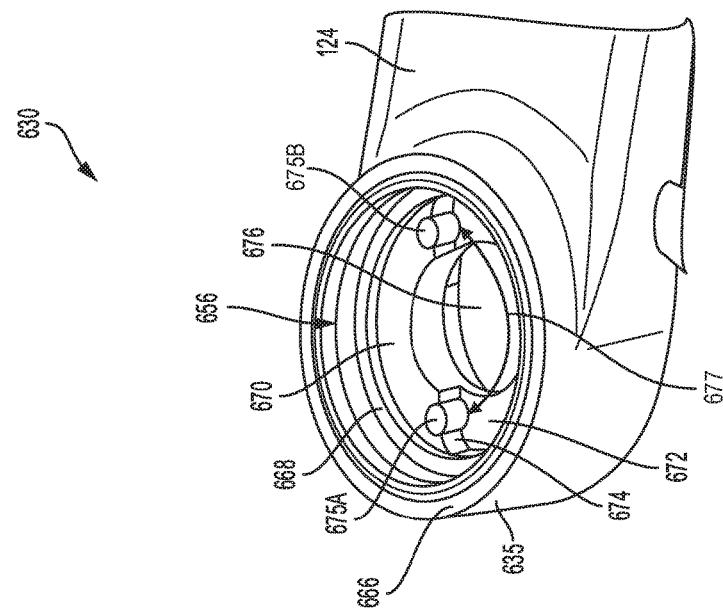
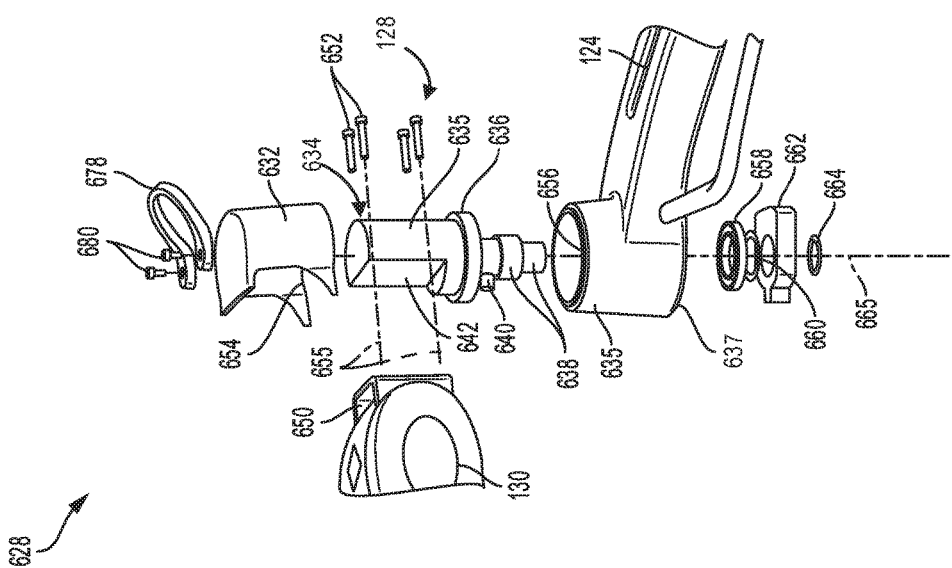

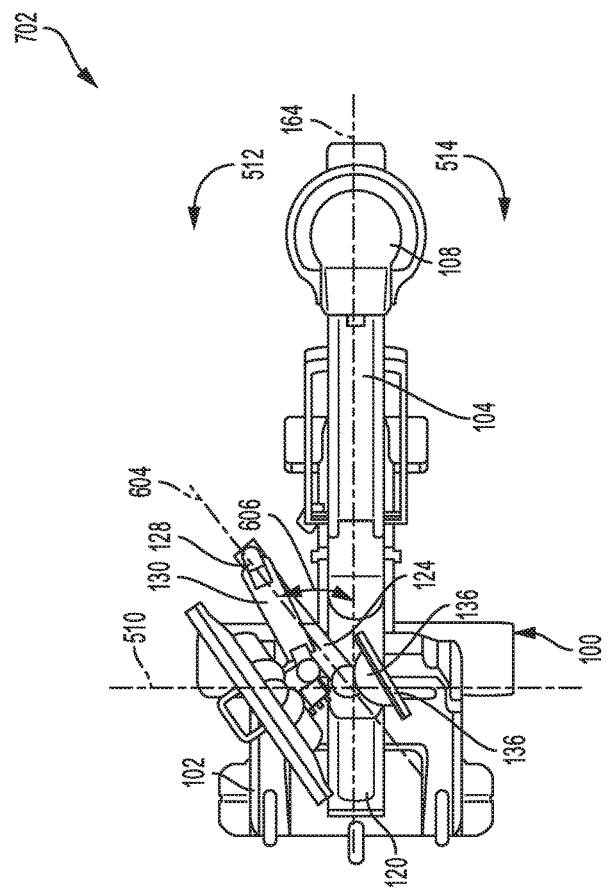
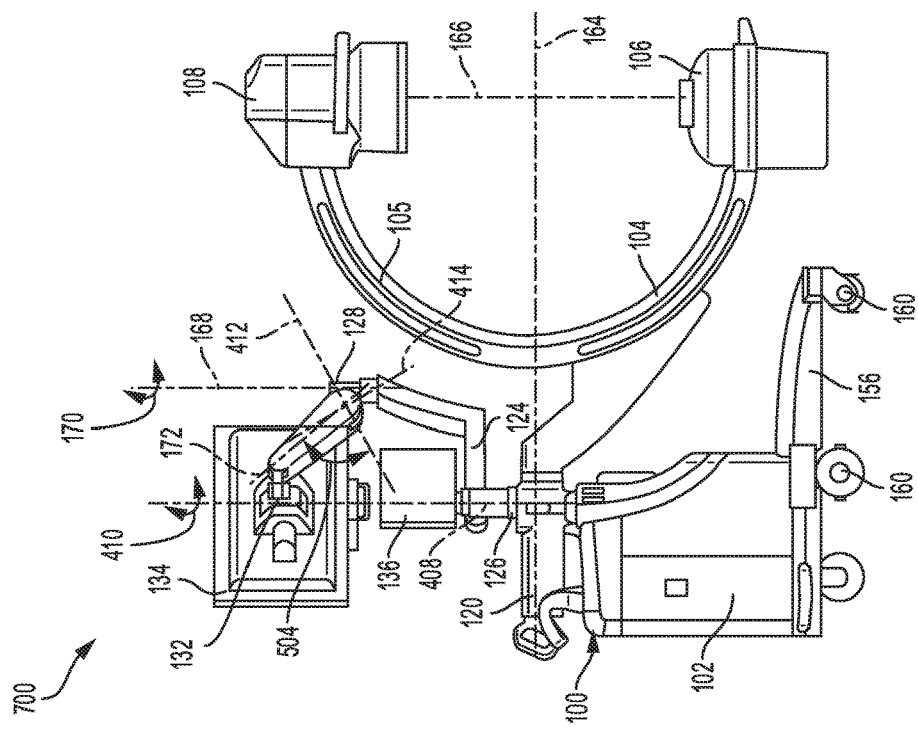
FIG. 7B
FIG. 7A

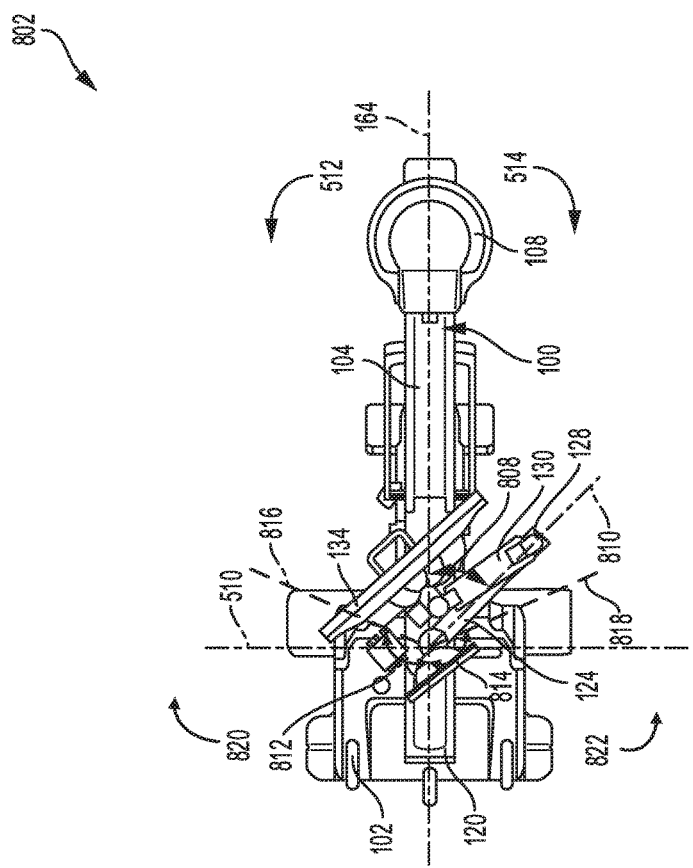

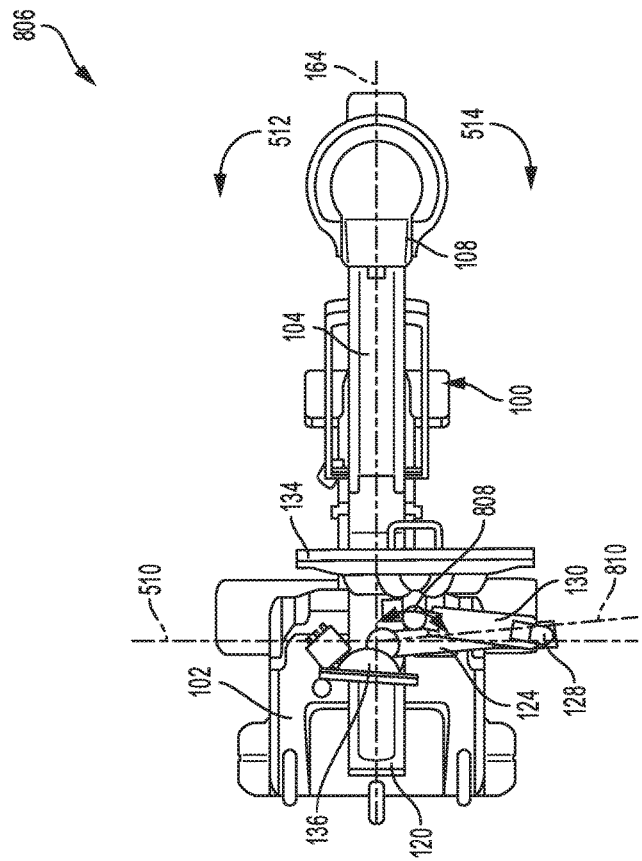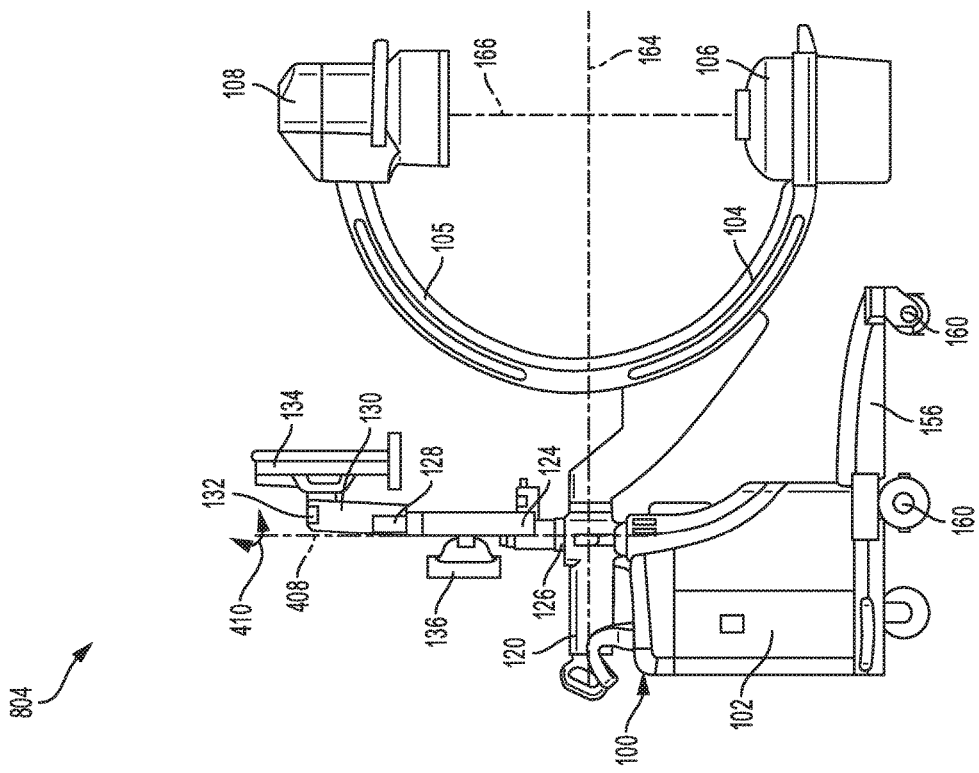
FIG. 8D
FIG. 8C

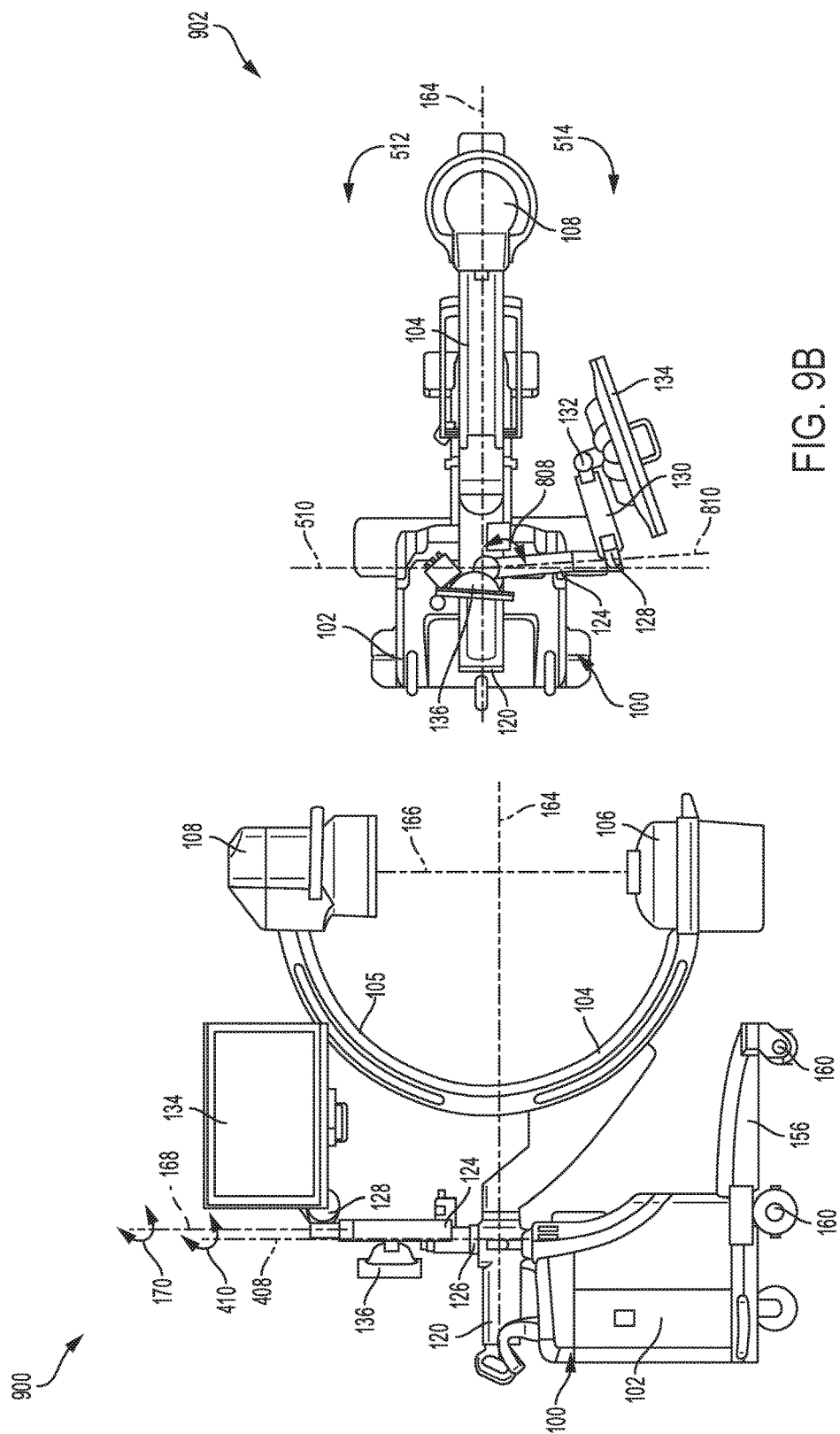

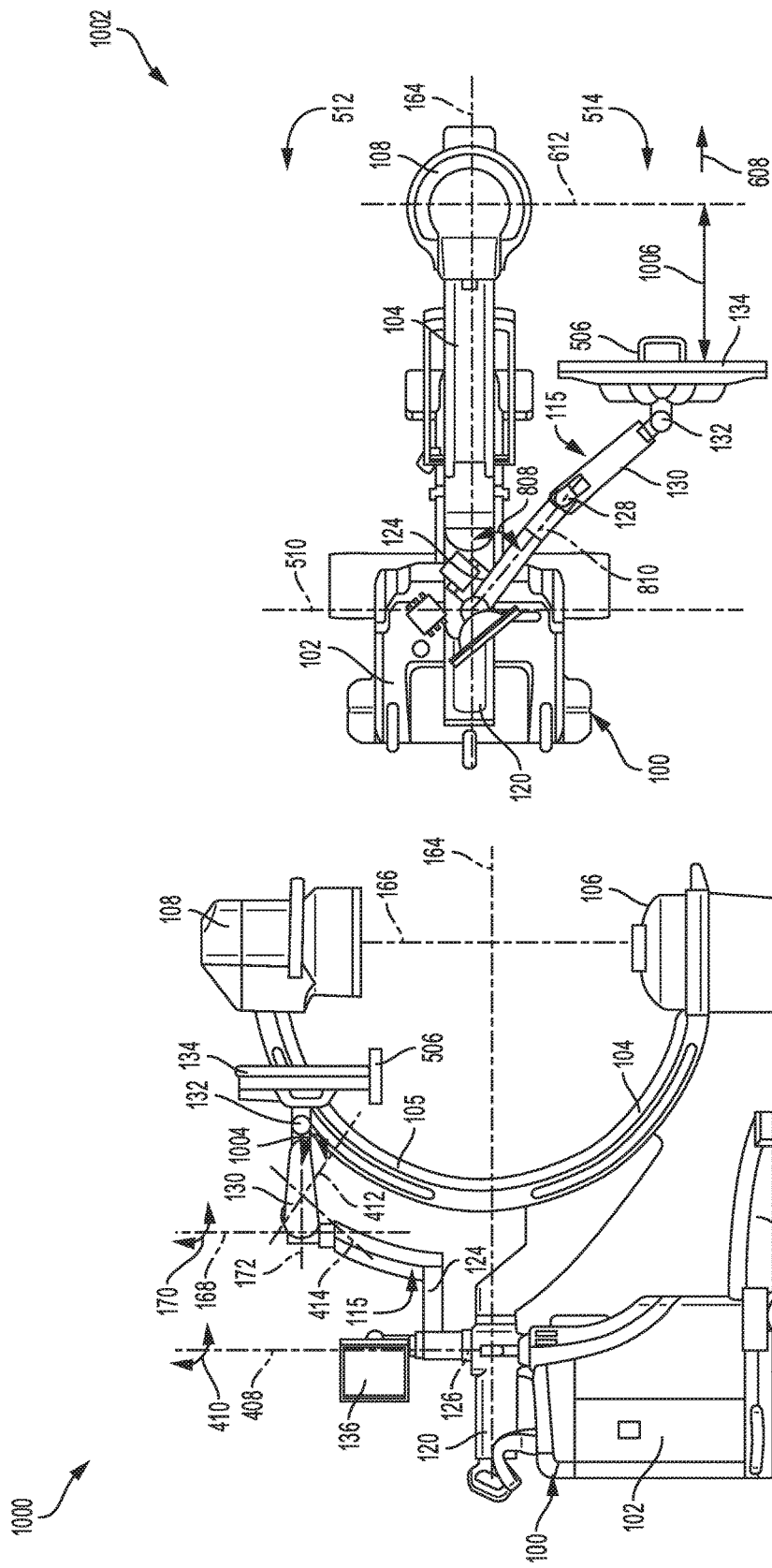

METHOD AND SYSTEMS FOR A COMPACT INTEGRATED MONITOR ARM FOR AN IMAGING SYSTEM

FIELD

Embodiments of the subject matter disclosed herein relate to a compact integrated arm for a display monitor of an imaging system.

BACKGROUND

Radiographic imaging systems may be used in various applications, including medical and industrial applications. In a medical environment, a radiographic imaging device may provide a non-invasive means of imaging tissue and bone of a patient. The imaging device may have the capability of capturing multiple images at designated intervals, and displaying the images in a sequence to create a single image of the object being examined.

The imaging device may comprise a swing arm coupled to a control unit, and a display monitor either attached to or arranged separated from the control unit. The swing arm (e.g., C-arm) may include an x-ray source positioned at one end of the arm, and a detector positioned on another end of the arm. A clearance may be provided between the x-ray source and detector to receive an object, such as a portion of the patient's body, which may be irradiated with radiation from the x-ray source. Upon irradiating the object, the x-ray radiation penetrates the object, before being captured by the detector on the other end of the object. By penetrating the object placed between the source and detector, the x-rays enable an image of the object to be captured and relayed to the display monitor, where the image may be displayed or stored and retrieved later.

BRIEF DESCRIPTION

In one embodiment, an imaging system may comprise: a base unit; a C-arm coupled to the base unit and including an x-ray source and detector positioned on opposite ends of a C-shaped portion of the C-arm; and a display monitor attached to the C-arm via an integrated arm, wherein the display monitor is movable between a first position on a first side of the C-arm, to a second position on a second side of the C-arm by traveling over a top of an upper half of the C-shaped portion.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIG. 4A shows a first three dimensional view of the imaging system, with the x-ray source positioned above the x-ray detector, and a display monitor placed in parked position.

FIG. 4B shows a second three dimensional view of the imaging system, with the x-ray source positioned below the x-ray detector, and the display monitor placed in the parked position.

FIG. 6A shows a side view of the imaging system, with the display monitor positioned at a first side of the C-arm.

FIG. 6B shows a plan view of the imaging system, with the display monitor positioned at the first side of the C-arm.

FIG. 6C shows an exploded view of the elbow joint connecting the articulating arm to the fixed arm.

FIG. 6D shows a three dimensional view of an annular portion of the fixed arm.

FIG. 7A shows a side view of the imaging system, with a fixed arm and an articulating arm oriented towards a first side of the C-arm to move the display monitor in a retracted position behind the C-arm.

FIG. 7B shows a plan view of the imaging system, with the fixed arm and articulating arm oriented towards the first side of the C-arm to move the display monitor in the retracted position behind the C-arm.

FIG. 8A shows a side view of the imaging system, with the display monitor positioned behind the C-arm and facing the first side of the C-arm.

FIG. 8B shows a plan view of the imaging system, with the display monitor positioned behind the C-arm and facing the first side of the C-arm.

FIG. 8C shows a side view of the imaging system, with the display monitor positioned behind the C-arm and facing an upper half of a C-shaped portion of the C-arm.

FIG. 8D shows a plan view of the imaging system, with the display monitor positioned behind the C-arm and facing the upper half of the C-shaped portion of the C-arm.

FIG. 9A shows a side view of the imaging system, with the display monitor positioned besides the C-arm and facing a second side of the C-arm.

FIG. 9B shows a plan view of the imaging system, with the display monitor positioned besides the C-arm and facing the second side of the C-arm.

FIG. 10A shows a side view of the imaging system, with the display monitor positioned at the second side of the C-arm.

FIG. 10B shows a plan view of the imaging system, with the display monitor positioned in the second side of the C-arm.

DETAILED DESCRIPTION

The following description relates to various embodiments of a compact integrated arm for a display monitor coupled to an imaging system.

Before further discussion of the imaging system and the compact integrated arm coupled to the display monitor, a brief description of the imaging device is disclosed herein.

During imaging operations, it may be desirable to capture multiple images of a portion of the patient's body from different positions without frequent repositioning of the patient. However, an articulating arm on an imaging device may not be adapted to move through a plurality of positions that allow multiple of images of the patient's body to be captured without moving the patient. Further, the imaging device may limit capacity for mobility during imaging operations. For example, a display monitor coupled to the articulating arm attached to a base unit, may require moving further back from the articulating arm when the display monitor is moved from one side of the arm to another side. In this example, adjusting the display monitor from one position to another may be time-consuming and may require undue effort from an operator. In another examples, the articulating arm attached to the display monitor may include a plurality of mechanical joints or locks that require unlocking and locking when the display monitor is moved from a first position to a second position. In this case, adjusting the imaging device during imaging operations may require additional effort and time.

Figure 1:
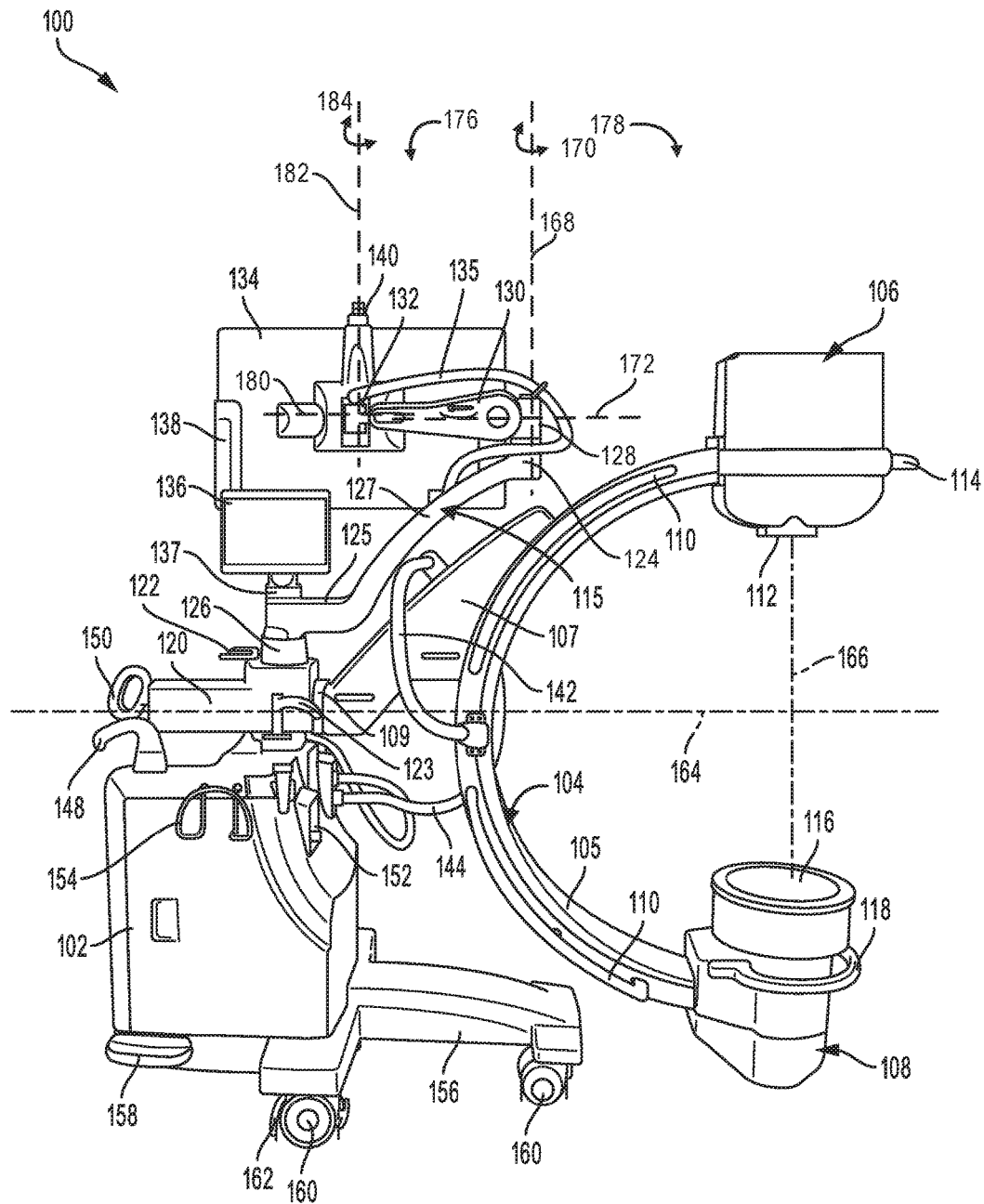
FIG. 1 shows a three dimensional view of an imaging system, having a C-arm with an x-ray source positioned above an x-ray detector.
Figure 2:
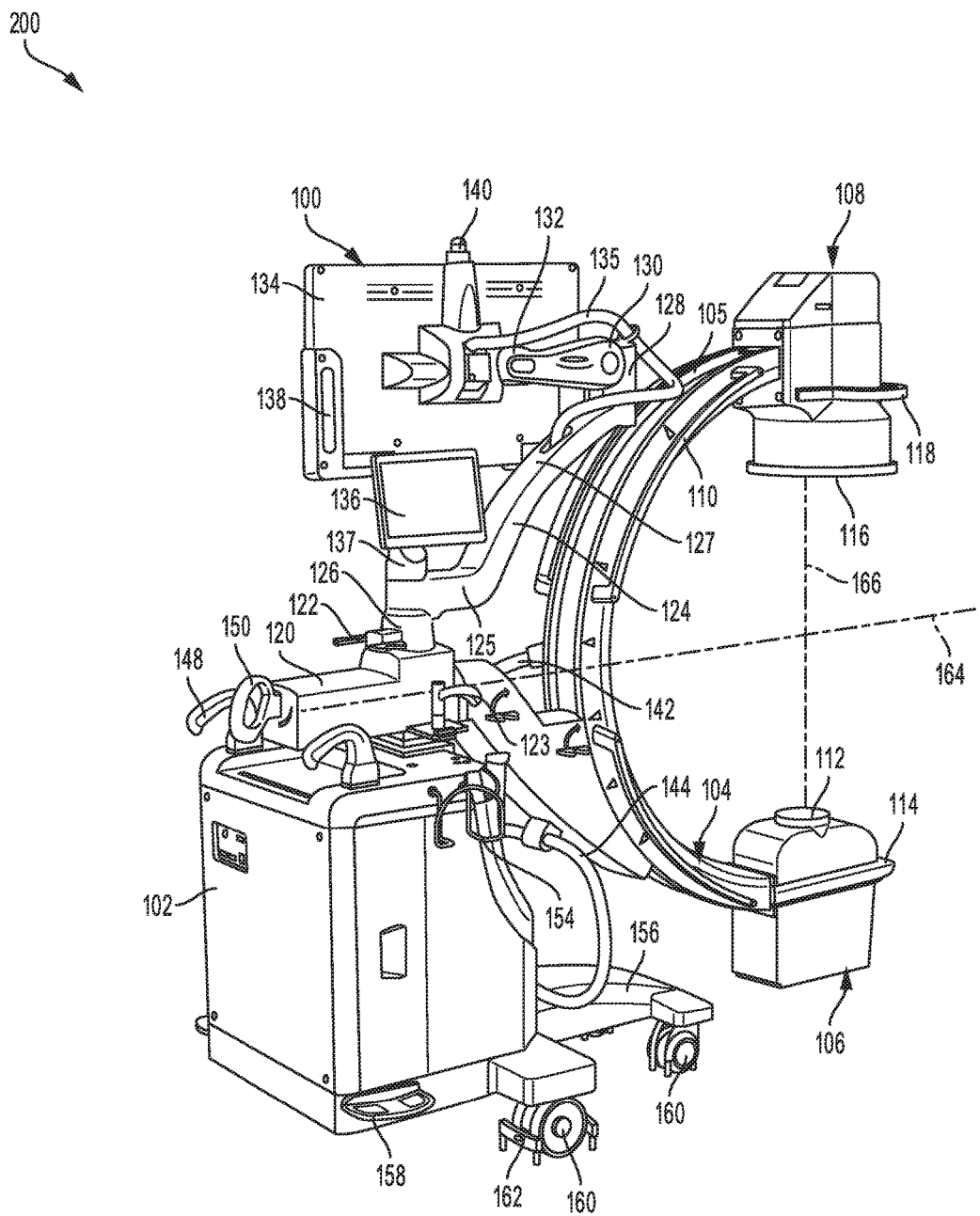
FIG. 2 shows a first alternative three dimensional view of the imaging system, having the C-arm with the x-ray source positioned below the x-ray detector.
Figure 3:
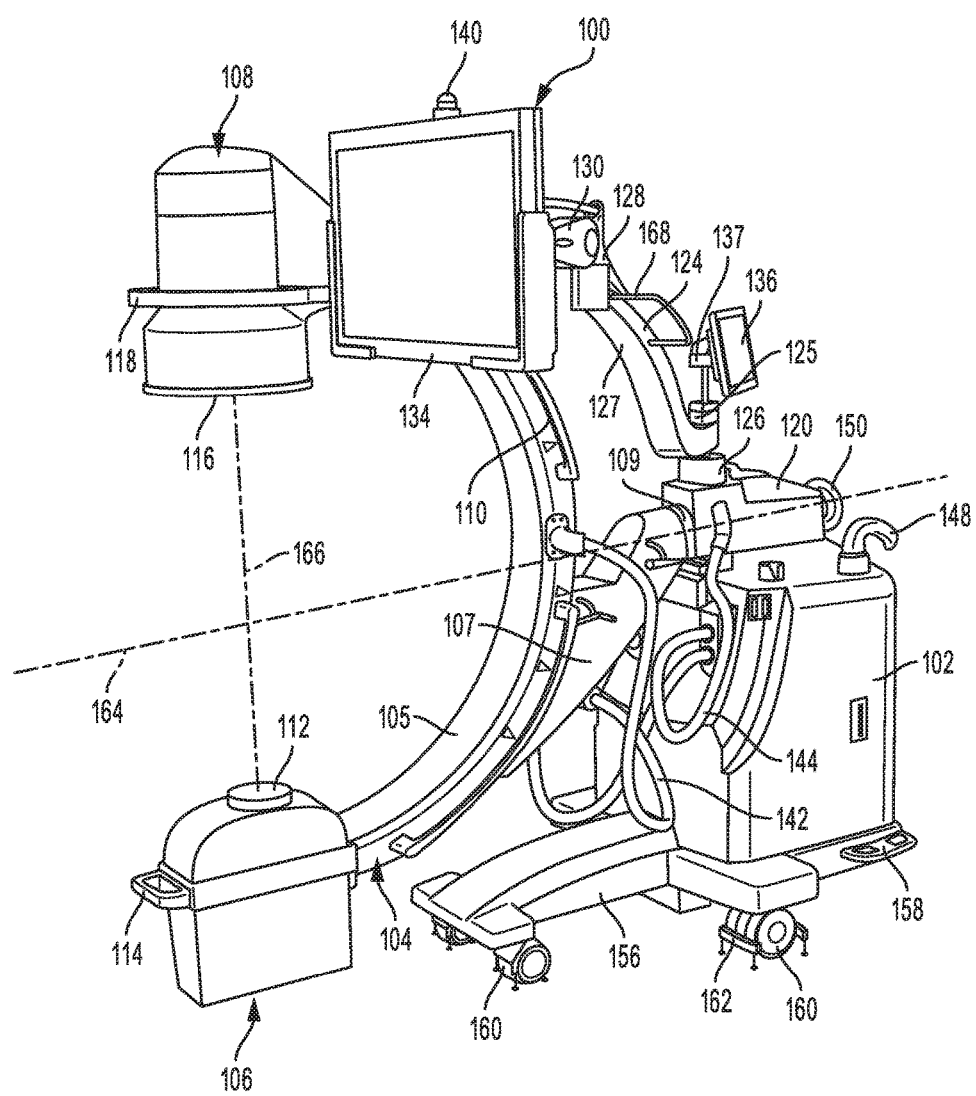
FIG. 3 shows a second alternative three dimensional view of the imaging system, having the C-arm with the x-ray source positioned below the x-ray detector.

As disclosed in FIGS. 1-3, an imaging system comprising a base unit, an integrated arm coupled to a display monitor and a C-arm having an x-ray source and detector positioned on opposite ends of a C-shaped portion of the C-arm may be provided to address some of the issues identified above. The C-arm may include an extended member coupled to the C-shaped portion of the arm on one end and coupled to a cross member via a rotatable joint at another end, the cross member coupled to the base unit to provide support to the C-arm. In this way, the C-arm may be advantageously adapted to rotate via the rotatable joint (about a central axis through a center of the C-shaped portion of the arm), to adjust position of the x-ray source and detector before or during imaging operations.

The integrated arm may include a fixed arm and an articulating arm coupled to one another via an elbow joint, as shown in FIGS. 1-3. One end of the fixed arm may be coupled to the cross member via a shoulder joint, and the other end of the fixed arm may be coupled to the elbow joint connected to the articulating arm. In this way, the fixed arm may include two offset joints, including the shoulder joint and elbow joint, arranged on opposite ends of the fixed arm. The shoulder joint may couple a straight portion of the fixed arm to the C-arm and the elbow joint may couple a curved portion of the fixed arm to the articulating arm, as shown in FIGS. 1-3.

The elbow joint may be configured to rotate through an angle of 0 to 180 degrees, for example. In this case, movement of the elbow joint allows the articulating arm coupled to the display monitor (via a wrist joint) to be adjusted through a wide range of positions. The wrist joint may be adapted for rotational movement, thereby allowing the display monitor to be oriented to a suitable position within the horizontal plane, as disclosed in FIGS. 4A-10B.

The imaging system may be placed in a parked position by moving the display monitor into a pocket attached to the fixed arm of the integrated arm, as shown in FIG. 4A. When placed in the parked position, the imaging system may be transported from one position to another by rolling the imaging system using a plurality of wheels coupled to a lower portion of the base unit, as shown in FIGS. 4A-B.

Figures 5A, 5B:
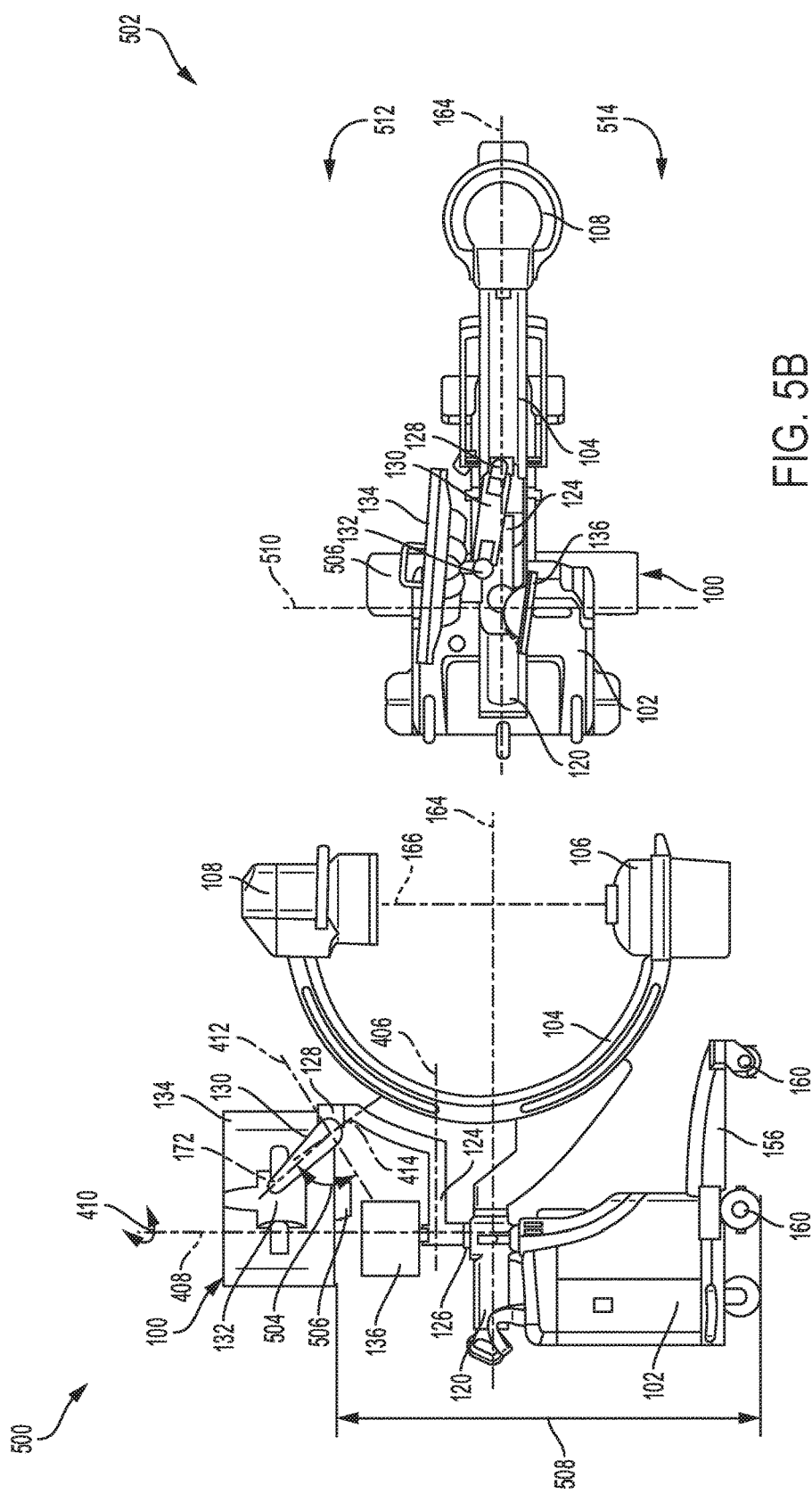
FIG. 5A shows a side view of the imaging system, with the x-ray source positioned below the x-ray detector, and the display monitor placed in an unlocked position behind a C-arm of the system.
FIG. 5B shows a plan view of the imaging system, with the display monitor placed in the unlocked position behind the C-arm of the system.

When the imaging system is in use, the display monitor may be adjusted from the parked position to an unlocked position behind the C-arm by orienting the articulating arm upward as shown in FIG. 5A. The fixed arm and elbow joint may be kept in prior positions disclosed in FIGS. 4A-B, while reorienting the articulating arm and display monitor in an upward direction as shown in FIG. 5A. In this case, the display monitor may be positioned behind the C-arm and facing a first side of the C-arm, as shown in FIG. 5B.

Figure 6E:
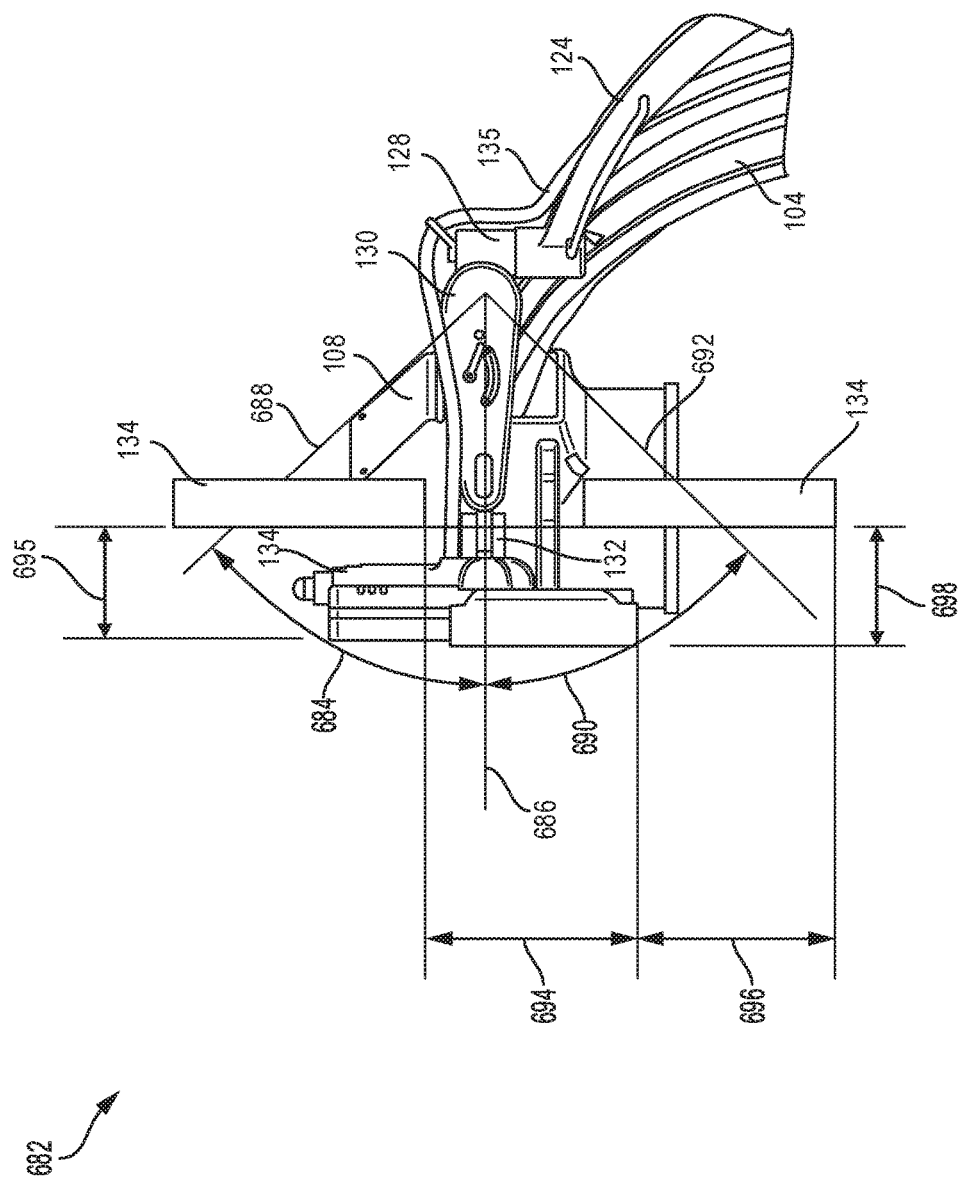
FIG. 6E shows a schematic view of the articulating arm adjusted through a plurality of positions to reorient the display monitor.

FIGS. 6A-6B show a side view and a plan view, respectively of the imaging system with the display monitor positioned on the first side of the C-arm. The display monitor may be moved from behind the C-arm to the first side of the C-arm by rotating the fixed arm via the shoulder joint, and adjusting the articulating arm via the elbow joint, and extending the articulating arm forward past the C-arm, as shown in FIG. 6A. The fixed arm may be reoriented by adjusting the arm via the shoulder joint which allows for rotation motion about a shoulder axis. For example, the fixed arm may be moved from a position where the straight portion of the arm lies above a central axis of the C-arm to a different position where the fixed arm is aligned along an arm center axis, as shown in FIG. 6B. The shoulder joint may include a single brake adapted to lock rotation of the shoulder joint, to place the fixed arm in a locked position. In this way, the fixed arm may be locked into a fixed position while the elbow joint and articulating arm are reoriented in a particular direction. The elbow joint may include a shaft having a stop screw, the shaft inserted in an opening (in an annular portion of the fixed arm) having a plurality of bumper pins, as shown in FIGS. 6C and 6D. The stop screw on the shaft may be used in conjunction with the bumper pins in the opening in the fixed arm to constrain the rotational movement of the elbow joint between a first and a second constrained position, for example. In this way, the elbow joint may not include a brake system, thereby providing the advantage of expeditiously adjusting position of the articulating arm without engaging or disengaging the brake system. The articulating arm coupled to the display monitor, may be adjusted through a plurality of positions to reorient the display monitor from one location to another location, as shown in FIG. 6E.

FIGS. 7A-B show a side view and a plan view, respectively of the imaging system with the display monitor placed in a retracted position behind the C-arm. The display monitor may be adjusted from the first side of the C-arm to the retracted position behind the C-arm by reorienting articulating arm via the elbow joint while the fixed arm may be kept in a fixed position, and moving the display monitor over the upper half of the C-shaped portion of the C-arm from the first side to the retracted position.

As shown in FIGS. 8A-D, the display monitor may be moved from the retracted position behind the C-arm to a position where the display monitor is partially positioned on the first and second side of the C-arm, by rotating the fixed arm via the shoulder joint without readjusting the elbow joint and articulating arm. The fixed arm may be adjusted outward and away from the C-arm via the shoulder joint which is rotated about the shoulder axis without readjusting the articulating arm coupled to the elbow joint, as shown in FIGS. 8A-B. The fixed arm may be further adjusted away from the C-arm without readjusting the articulating arm and elbow joint, as shown in FIG. 8C-D. By rotating the fixed arm across the top half of the C-shaped portion of the C-arm towards the second side of the C-arm, the display monitor is moved over the top half of the C-shaped portion without swinging the display monitor around a back side of the base unit connected to the C-arm.

FIGS. 9A-B show a side view and a plan view, respectively of the imaging system with the display monitor facing the second side of the C-arm. The display monitor may be moved from the retracted position behind the C-arm to the second side of the C-arm by rotating the articulating arm via the elbow joint while the fixed arm is kept in a fixed position by locking brakes on the shoulder joint.

FIGS. 10A-B show a side view and plan view, respectively of the imaging system, with the display monitor positioned on the second side of the C-arm and facing a direction of an operator of the imaging system. The display monitor may be extended forward and past the C-arm to the second side of the C-arm by adjusting positions of the fixed arm via the shoulder joint, and reorienting the articulating arm via the elbow joint. Further, the display monitor may be reoriented to face a direction of the operator of the imaging system via the wrist joint. In this way the display monitor may be reoriented by rotating the fixed arm inward toward the C-arm via the shoulder joint while rotating the articulating arm further inward and towards the C-arm via the elbow joint to move the display monitor into the extended position on the second side of the C-arm.

Figure 11:
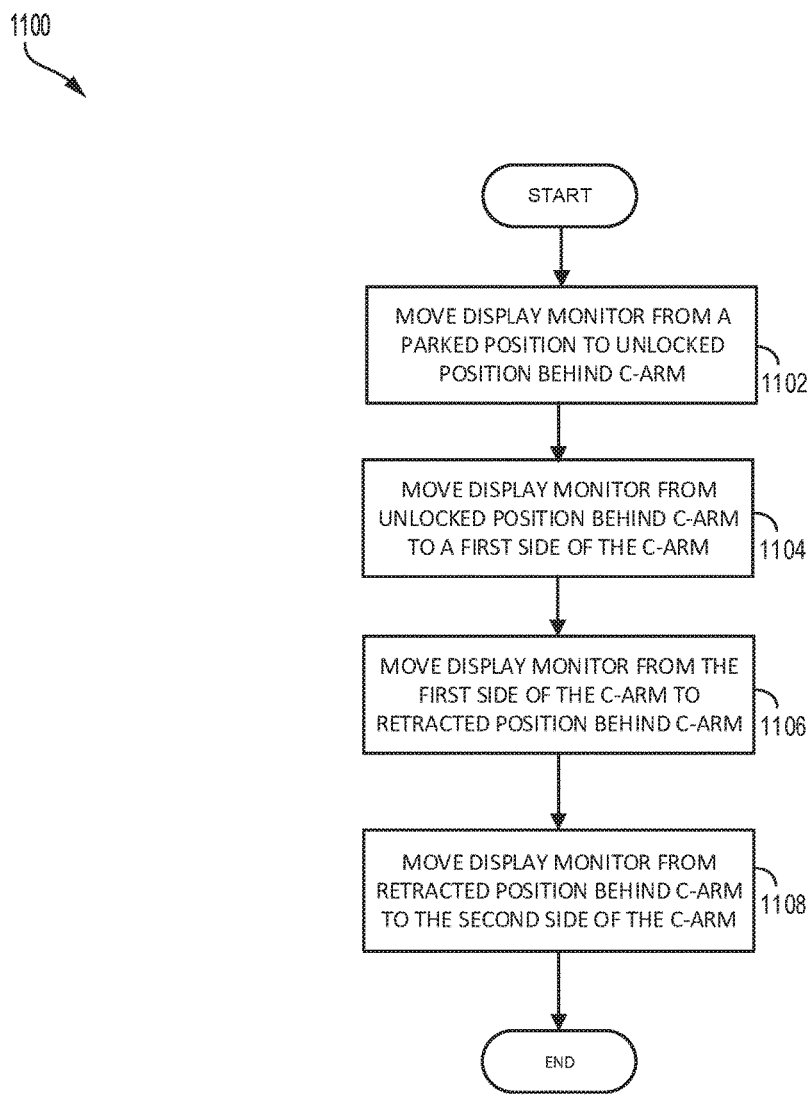
FIG. 11 shows a method for adjusting the display monitor of the imaging system from the first side of the C-arm to the second side of the C-arm.

FIG. 11, discloses a method for repositioning the display monitor coupled to the integrated arm of the imaging system from the first side of the C-arm to the second side of the C-arm. In this way, the display monitor may be moved across the top half of the C-shaped portion of the C-arm, from the first side of the C-arm to the second side of the C-arm without swinging the display monitor around a back side of the base coupled to the C-arm.

Turning to FIG. 1, a three dimensional view of an imaging system 100, having a C-arm 104 with an x-ray source 106 positioned directly above an x-ray detector 108, is disclosed. The imaging system 100 also includes a base unit 102, an integrated arm 115, a display monitor 134 and a display tablet 136. The base unit 102 may include a vertical rod 123, one or more push handles 148, a switch 152 and a side pocket 154. A base portion 156 of the base unit 102 may include a side component 158 and a plurality of wheels 160 that allow the imaging system 100 to be transported from one position to another. Each wheel 160 may include a brake 162 that allows the wheel to be locked into a fixed position, to prevent movement of the imaging system 100.

As shown in FIG. 1, the C-arm 104 may include a C-shaped portion 105 connected to an extended portion 107 coupled to a cross member 120 via a rotatable joint 109. The cross member 120 may be mounted to the base unit 102 which may provide support to the C-arm 104. A lock handle 150, may be adjusted to unlock the C-arm 104, to allow the C-arm to rotate via the rotatable joint 109. As an example, the C-arm 104 may be configured to rotate at least 180 degrees in each direction via the rotatable joint 109 coupling the C-shaped portion 105 to the extended portion 107 of the C-arm 104. In one example, the C-arm 104 may be rotatable (via the rotatable joint 109) about a central axis 164 of the C-shaped portion 105, to adjust the x-ray source 106 and detector 108 (positioned on opposite ends of the C-shaped portion of the C-arm 104 along a vertical axis 166) through a plurality of positions (e.g., at least switch vertical positions, top and bottom, between the detector and x-ray source). The C-shaped portion 105 of the C-arm 104 may include a plurality of handle bars 110 that may be held when rotating the C-arm via the rotatable joint 109, to adjust positions of the x-ray source 106 and detector 108 before or during operation of the imaging system 100. The x-ray source 106 may include an outer cap 112 and a handle 114. The outer cap 112 may be adapted to direct x-ray radiation towards an outer face 116 of the detector 108. A curved handle 118, provided on the detector 108, may be used to adjust position of the detector 108 with respect to the x-ray source 106.

The integrated arm 115 may include a fixed arm 124 and an articulating arm 130 coupled to one another via an elbow joint 128. One end of the fixed arm 124 may couple the cross member 120 adjacent to a shoulder joint 126, and the other end of the fixed arm 124 may couple the elbow joint 128 connected to the articulating arm 130. In this way the fixed arm 124 may include two offset joints, including the shoulder joint 126 and elbow joint 128, arranged on opposite ends of the fixed arm 124, wherein the shoulder joint 126 of the two offset joints couples a straight portion 125 of the fixed arm to the C-arm 104 and the elbow joint 128 of the two offset joints couples a curved portion 127 of the fixed arm to the articulating arm 130. A brake handle 122 may be provided adjacent to the shoulder joint 126. As an example, the brake handle 122 may be adjusted to a first position to lock the shoulder joint 126, thereby allowing the articulating arm 130 to be reoriented in a particular direction while keeping the fixed arm 124 in a fixed position. In another example, the brake handle 122 may be adjusted to a second position to unlock the shoulder joint 126, thereby allowing the fixed arm 124 to be reoriented in a particular direction while keeping the articulating arm 130 in a fixed position. The elbow joint 128 may be configured to rotate about an elbow rotational axis 168 in a direction shown by double arrows 170, thereby allowing the articulating arm 130 coupled to the display monitor 134 to be adjusted through a wide range of positions. For example, the elbow joint 128 may be adapted to rotate through an angle ranging from 10 to 190 degrees. In this way, the articulating arm 130 may be rotated via the elbow joint 128 to move the display monitor 134 from a retracted position behind the C-arm 104 to a different position on either side of the C-arm 104, where the display monitor 134 is positioned adjacent the x-ray source 106. The articulating arm 130 may be coupled to the display monitor 134 via a wrist joint 132 positioned at one end of the articulating arm. The wrist joint 132 may be adapted to rotate about a wrist rotational axis 182, as shown by double direction arrows 184, thereby allowing the display monitor 134 to be oriented in a plurality of positions within a horizontal plane which may be parallel to a wrist axis 180 and perpendicular to the wrist rotational axis 182. The display monitor 134 may include a plurality of side casings 138 and an antenna 140. The plurality of side casings 138 may be adapted to hold and protect the display monitor 134.

During an imaging operation, a portion of a patient's body placed in a clearance (e.g., gap) formed between the x-ray source 106 and detector 108, may be irradiated with radiation from the x-ray source. The radiation may penetrate the portion of the patient's body being irradiated, and travel to the detector 108 where the radiation is captured. By penetrating the portion of the patient's body placed between the x-ray source 106 and detector 108, an image of the patient's body is captured and relayed to the display monitor 134 via a connection line (e.g., electrical connection line) 135, where the image is displayed or stored and retrieved later. In one example, the display monitor may display images taken and processed by the imaging system, as they are taken and during the imaging procedure (e.g., in real-time). Further, a display tablet 136 coupled to a vertical member 137 connected to the fixed arm 124 at the shoulder joint 126, may be used to enter instructions in the imaging system 100 or display images of the patient's body taken by the x-ray source 106. An example of instructions entered into the display tablet 136 may include x-ray source activation, source voltage/current, source rotation, image display, image storing, etc.

The base unit 102 may include a control and computing unit (not shown) that processes instructions or commands sent from the display tablet 136 during operation of the imaging system 100. The base unit 102 may also include an internal power source (not shown) that provides electrical power to operate the imaging system 100. Alternatively, the base unit 102 may be connected to an external electrical power source to power the imaging system 100. A plurality of connection lines 142-144, may be provided to transmit instructions or data between the x-ray source 106, detector 108 and the control and computing unit in the base unit 102, for example. In alternative examples, input commands and data may be transmitted between the x-ray source 106, detector 108 and the base unit 102 via a wireless connection or network, thereby advantageously obviating the need for connection lines or cables. In other examples, the plurality of connection lines 142-144 may transmit electrical power from an electrical power source to the x-ray source 106 and detector 108.

In this way, the imaging system 100 may comprise: the base unit 102; the C-arm 104 coupled to the base unit 102 and including an x-ray source 106 and detector 108 positioned on opposite ends of a C-shaped portion 105 of the C-arm 104; and the display monitor 134 attached to the C-arm 104 via an integrated arm, wherein the display monitor 134 is movable between a first position on a first side of the C-arm 104, to a second position on a second side of the C-arm 104 by traveling over a top of an upper half of the C-shaped portion 105. As an example, the integrated arm may include the fixed arm 124 and articulating arm 130 coupled to one another via the elbow joint 128. In further examples, the integrated arm includes three movable joints offset from one another along the integrated arm. In one example, the three movable joints may include the shoulder joint 126, elbow joint 128 and wrist joint 132.

Referring to FIGS. 2-3, a first alternative three dimensional view 200 and a second alternative three dimensional view 300, respectively of the imaging system 100 is disclosed. The imaging system 100 is shown with the C-arm 104 rotated to a position where the x-ray source 106 is positioned directly below the detector 108.

The C-arm 104 may be adjusted from a first position (the x-ray source 106 is positioned directly above the detector 108) to a second position where the x-ray source 106 is positioned directly below the detector 108, by rotating the C-arm via the rotatable joint 109. When adjusted to the second position, the x-ray source 106 may be positioned below the central axis 164 of the C-shaped portion 105 of the C-arm 104, and the detector 108 may be positioned above the central axis 164. During operation of the imaging system 100, the radiation emitted from the x-ray source 106 may be directed upward and toward a portion of the patient's body positioned (between the source and detector). The radiation may penetrate the portion of the patient's body and may be received by the detector 108 positioned directly above the x-ray source 106. The detector 108 may include an image receptor that captures image data of the patient's body and transmits the data to the computing unit in the base unit 102, where the data is processed to produce an image of the patient's body which is relayed to the display monitor 134 and display tablet 136 for viewing by an operator of the imaging system or a medical specialist.

A position of the display monitor 134 may be adjusted from a first position where the display monitor is positioned behind the C-arm 104, as shown in FIG. 2, to a second position at a first side of the C-arm, as shown in FIG. 3, by adjusting the fixed arm 124 via the shoulder joint 126, and rotating the articulating arm 130 via the elbow joint 128. When adjusted to the first position, the curved portion 127 of the fixed arm 124 approximately follows a radius of curvature of a top half of a C-shaped portion 105 of the C-arm 104. As an example, when the display monitor 134 is adjusted to a parked position, the curved portion 127 of the fixed arm curves along a portion of, but offset from, the top half of the C-shaped portion 105 of the C-arm 104. In other examples, the shoulder joint 126 and elbow joint 128 may be adjusted by rotating the articulating arm 130 outward and away from the C-arm 104 via the elbow joint 128; and rotating the fixed arm 124 inward toward the C-arm 104 via the shoulder joint 126 while rotating the articulating arm 130 further outward and away from the C-arm 104 via the elbow joint 128 to move the display monitor 134 into an extended position on a first side of the C-arm.

In this way, the fixed arm 124 and articulating arm 130 coupled to the elbow joint 128 may be adjusted to move the display monitor 134 from the first position behind the C-arm 104 to the second position at the first side of the C-arm. When adjusted to the second position, the display monitor 134 may be positioned at a threshold distance that allows an operator to visually inspect displayed images of the patient's body taken by the imaging system 100. In this way, the fixed arm 124 and articulating arm 130 may be adjusted to orient the display monitor 134 to a position closest to the operator, while minimizing amount of space required to orient both arms.

Referring to FIGS. 4A-B, a first three dimensional view 400 and a second three dimensional view 402, respectively of the imaging system 100, with the display monitor 134 placed in a parked position is disclosed. The display monitor 134 is placed in the parked position by placing the monitor in a pocket 404. When placed in the parked position, the imaging system 100 may be transported from one position to another by rolling the system via the plurality of the wheels 160 coupled to the base portion 156.

The C-arm 104 may be positioned in a first position, where the x-ray source 106 is positioned directly above the detector 108, as shown in FIG. 4A. Alternatively, the C-arm 104 may be adjusted from the first position to a second position by rotating the arm via the rotatable joint 109, as shown in FIG. 4B. When adjusted to the second position, the x-ray source 106 may be positioned directly below the detector 108. The imaging system 100 may be transported while the C-arm 104 is adjusted to either the first or second position. The display monitor 134 may be placed in the parked position when the straight portion of the fixed arm 124 is aligned along an arm axis 406, and the elbow joint 128 is rotated such that the articulating arm 130 lies in along a first elbow axis 412 positioned perpendicular to a second elbow axis 414. The shoulder joint 126 may rotate about shoulder axis 408, as shown by double arrows 410, such that the straight portion of the fixed arm 124 lies along the arm axis 406.

When articulating arm 130 is aligned along the first elbow axis 412, the display monitor 134 may be adjusted to fit in the pocket 404 that secures the display monitor in a fixed position, as shown in FIG. 4A. As an example, the pocket 404 may be an adequately sized opening (enclosed by a curved rod 405) formed on either side of the display monitor 134. When placed in the parked position, the display monitor 134 may be positioned behind the C-arm 104 at a height 416, as shown in FIG. 4B. In this way, fixed arm 124 and articulating arm 130 may be adjusted to orient the display monitor 134 such that the monitor is placed in the parked position, to allow the imaging system 100 to be transported from one position to another position while minimizing space occupied by the display monitor 134 and both arms. A brake (not shown) on the shoulder joint 126 may be locked to keep the fixed arm 124 in a fixed position when the display monitor 134 is placed in the parked position. Further, the elbow joint 128 may be adjusted to a position that minimizes or reduces movement of the articulating arm 130 when the display monitor 134 is oriented in the parked position. The elbow joint 128 may be locked into position via a friction force provided by the display monitor 134 attached to the articulating arm 130 coupled to the elbow joint. In this case, a brake mechanism is not provided on the elbow joint 128, since the elbow joint may be locked into a fixed position via the friction force provided by the display monitor 134. In this way, the imaging system 100 may be transported from a first position to a second position while the fixed arm 124 and articulating arm 130 are kept in fixed positions by locking (e.g., via the brake mechanism) the shoulder joint 126 and by the friction force of the elbow joint 128.

Referring to FIGS. 5A-B, a side view 500 and a plan view 502, respectively of the imaging system 100 with the display monitor 134 placed in an unlocked position is disclosed. The display monitor 134 may be placed in the unlocked position by moving the display monitor out of the pocket (such as pocket 404 shown in FIG. 4A). The display monitor 134 may include a handle bar 506 for orienting the monitor in a particular orientation via the wrist joint 132.

The display monitor 134 may be adjusted from the parked position (where the articulating arm 130 is positioned along the first elbow axis 412) to the unlocked position by orienting the articulating arm 130 through an angle 504, defined between the first elbow axis 412 and the arm center line 172. The fixed arm 124 and elbow joint 128 may be kept in prior orientation positions disclosed in FIGS. 4A-B, while the articulating arm 130 is adjusted to reorient the display monitor 134. As an example, the fixed arm 124 may remain aligned along arm axis 406, and the elbow joint 128 may remain facing the display monitor 134, while the articulating arm 130 is adjusted. The angle 504 of the articulating arm 130 may range from 0 to 180 degrees, for example. When the articulating arm 130 is aligned along the first elbow axis 412, the angle 504 may be equal to zero degrees. A height 508 of the display monitor 134 may be adjusted by varying a magnitude of the angle 504 of the articulating arm 130. For example, the articulating arm 130 may be adjusted from a first angle to a second angle (where the second angle is larger than the first angle) to increase the height of the display monitor 134. In this example, the display monitor 134 may be at a first height when the articulating arm 130 is adjusted to the first angle, and at a second height when the articulating arm 130 is adjusted to the second angle, where the second height is greater than the first height. In this way, the display monitor 134 may be adjusted through a wide range of heights to suit needs of different operators of the imaging system 100. The wrist joint 132 may be adjusted to orient the display monitor 134 in a particular direction.

When the display monitor 134 is adjusted to the unlocked position, the fixed arm 124 may be aligned along the central axis 164 of the C-shaped portion 105 of the C-arm 104, the central axis positioned perpendicular to an axis 510 of the imaging system 100, as shown in FIG. 5B. The display monitor 134 may be positioned behind the C-arm 104, adjacent to the display tablet 136 when adjusted to the unlocked position.

Referring to FIGS. 6A-B, a side view 600 and a plan view 602, respectively of the imaging system 100 with the display monitor 134 positioned at the first side 512 of the C-arm 104 is disclosed. The display monitor 134 may be moved from a position behind the C-arm 104 to a front position besides the C-arm 104 by rotating the fixed arm 124 via the shoulder joint and adjusting the articulating arm 130 via the elbow joint 128.

The fixed arm 124 is reoriented by adjusting the fixed arm via the shoulder joint 126 which is rotated about the shoulder axis 408, as shown by double arrows 410 disclosed in FIG. 6A. As an example, the fixed arm 124 may be moved from a position where a straight portion of the arm lies along the central axis 164 of the C-shaped portion 105 of the C-arm 104 to a different position where the fixed arm 124 may be aligned along an arm center line 604, as shown in FIG. 6B. In this case, the fixed arm 124 may define an angle 606 between the central axis 164 and the arm center line 604. As an example, angle 606 may be equal to zero degrees when the fixed arm 124 is aligned with the central axis 164, as shown in FIG. 5B. In other examples, angle 606 may be greater than or less than zero degrees if the fixed arm 124 is not aligned with the central axis 164. In one example, the fixed arm 124 may be rotatable via the shoulder joint 126 such that angle 606 has a range from 0 to 90 degrees when the fixed arm 124 rotates away from the central axis 164 and towards the first side 512 of the C-arm. The shoulder joint 126 may include a single brake (e.g., single brake 122 on the shoulder joint and the rest of the integrated arm as shown in FIG. 1) coupled to the shoulder joint and adapted to lock rotation of the shoulder joint. In this way, the fixed arm 124 may be locked into a fixed position, such that the articulating arm 130 may be adjusted by rotating the elbow joint 128. The elbow joint 128 may not include a brake system, and thus the fixed arm may include only the single brake at the shoulder joint, thereby providing the advantage of expeditiously adjusting position of the articulating arm 130 without engaging or disengaging the brake system and adjusting the display monitor more quickly due to a reduced number (e.g., only one) of brakes on the integrated arm.

After adjusting the fixed arm 124, the elbow joint 128 may be rotated about the elbow rotational axis 168 to orient the articulating arm 130 and display monitor 134, as shown by the double arrows 170 in FIG. 6A. For example, the elbow joint 128 may be adapted to rotate through an angle 624 ranging from 10 to 190 degrees, as shown in FIG. 6B. When the elbow joint 128 is adjusted to a first constrained position, the angle 624 may have a value of 10 degrees, for example. In this case, the fixed arm 124 may not be aligned with the articulating arm 130 coupled to the elbow joint 128. When the elbow joint 128 is adjusted to the first constrained position, the articulating arm 130 may define an angle 626 between the arm center lines 604 and 605. In one example, the angle 626 may have a value of 10 degrees when the elbow joint 128 is adjusted to the first constrained position. In another example, the elbow joint 128 may be adjusted to a second constrained position, where the angle 624 has a value of 190 degrees. The elbow joint 128 may never rotate beyond the first and second constrained positions, since the angle 624 is always equal to or greater than 10 degrees but less than or equal to 190 degrees, thereby obviating the need for a brake on the elbow joint. In this case, the elbow joint 128 may not extend beyond the first and second constrained positions, thereby expediting the adjusting of the articulating arm 130 when reorienting the display monitor 134 from one position to another. In this way, the articulating arm 130 may be rotated via the elbow joint 128 to move the display monitor 134 from a position behind the C-arm 104 to the first side 512 of the C-arm 104, as shown in FIG. 6B.

The elbow joint 128 may be reoriented from a first position where the elbow joint faces away from the C-arm 104 to a second position where the elbow joint faces an upper half of the C-shaped portion 105 of the C-arm 104. Subsequently, the articulating arm 130 may be adjusted from a first position where the arm may be facing upward and away from the C-arm 104 to a second position where the articulating arm faces the upper half of the C-shaped portion 105 of the C-arm 104. In this case, the articulating arm 130 may define an angle 603 between the first elbow axis 412 and arm center line 172. In this example, angle 603 may be smaller than the angle 504 of the articulating arm 130 disclosed above in FIG. 5A. In this way, the articulating arm 130 may be adapted to pivot at the elbow joint 128 and wherein the articulating arm 130 may be coupled to the display monitor 134 via the wrist joint 132. As an example, the wrist joint 132 may be rotated about the wrist rotational axis 182 such that the display monitor 134 faces a direction of an operator (e.g. in a direction of arrow 608 as shown in FIG. 6B). In one example, the wrist joint 132 may be adapted to rotate the display monitor 134 through a first angle 616 defined between the arm center line 172 and axis 612 on a first side 620 of the arm center line 172, and a second angle 618 defined between the arm center line 172 and axis 612 on a second side 622 of the arm center line 172. In another example, the first angle 616 may range from 0 to 90 degrees, and the second angle 618 may range from 0 to −90 degrees, where each of the first angle 616 and second angle 618 is equal to zero degrees along the arm center line 172.

When positioned at the first side 512 of the C-arm, the display monitor 134 may be at a first distance 610 from axis 612, adjacent to an operator (not shown) operating the imaging system 100. In one example, the distance 610 of the display monitor 134 from axis 612 may be 337 cm. In other examples, the distance 610 of the display monitor 134 from the axis 612 may range from 190 mm to 898 mm. The display monitor 134 may be adjusted to an appropriate distance within the above range by moving the display monitor either towards or away from the operator. For example, the display monitor 134 may be moved to a distance that allows the operator to visually inspect images on the display monitor with ease. In this case the display monitor 134 may be moved through a plurality of distances that allow the operator of the imaging system 100 to visually inspect images on the display monitor with ease.

In this way the display monitor 134 may be reoriented by rotating the fixed arm 124 inward toward the C-arm 104 via the shoulder joint 126 while rotating the articulating arm 130 further inward and towards the C-arm 104 via the elbow joint 128 to move the display monitor 134 into the extended position on the first side 512 of the C-arm 104.

Referring to FIGS. 6C and 6D, an exploded view 628 of the elbow joint 128 and a three dimensional view 630 of an annular portion 635 of the fixed arm 124, respectively is disclosed. The articulating arm 130 is coupled to the fixed arm 124 via the elbow joint 128 on one end, and coupled to the display monitor (e.g., display monitor 134, shown in FIGS. 6A and 6B) on the other end. The elbow joint 128 may include a cover 632, a shaft 634, and a handle 678, the shaft 634 adapted to fit inside an opening 656 in the fixed arm 124. The shaft 634 may include a first annular portion 635 coupled to a second annular portion 638 via a circular ring 636. The second annular portion 638 includes a slot (not shown) which accommodates a fastener 640 that may be adjusted to control a range of rotational movement of the shaft 634 when coupled to the fixed arm 124, thereby restricting the movement of the elbow joint 128 to a predetermined distance defined by the angle 624 shown in FIG. 6B. The opening 656 in the annular portion 635 of the fixed arm 124 includes a circular edge 668, a first curved portion 670, a second curved portion 672 and an inner slot 676. The first curved portion 670 may include side sections 674 that have recessed slots sized to accommodate bumper pins 675A and 675B. The first curved portion 670 may be formed at a higher elevation compared to the second curved portion 672.

The elbow joint 128 may be assembled by extending the shaft 634, along elbow axis 665, and inserting the shaft 634 into the opening 656 in the annular portion 635 of the fixed arm 124. When inserted in the opening 656, the second annular portion 638 of the shaft 634 may fit inside the inner slot 676 formed in a central section of the first and second curved portions 670 and 672. The circular edge 668 which encloses the first curved portion 670 and second curved portion 672, may be adapted to receive the circular ring 636, when the shaft 634 is coupled to the fixed arm 124. The first annular portion 635 of the shaft 634 may extend out of the opening 656 when the shaft 634 is inserted in the opening 656 in the annular portion 635 of the fixed arm 124.

A recessed section 642 formed on the first annular portion 635, may be adapted to receive an extended portion 650 of the articulating arm 130 which is secured to the shaft 634 using a plurality of fasteners 652 extended through openings (not shown) in the first annular portion 635. The plurality of fasteners 652 may be further extended through corresponding openings in the extended portion 652 of the articulating arm 130, each corresponding opening in the extended portion 652 aligned with openings in the shaft 634 along axes 655. Subsequently, the cover 632 may be placed over the first annular portion 635, with a side opening 654 in the cover 632 facing the extended portion 650 of the articulating arm 130. When installed, the cover 632 may be in face sharing contact with a circumferential surface 666 of the annular portion 635. The handle 678 may be secured to a top surface of the cover 632 via a plurality of fasteners 680. As an example, the fasteners 680 may be screws extended through openings in the handle 678, and further extended through openings in the cover 632, to secure the handle 680 to the cover 678. A first sealing ring 658, a second sealing ring 660, a third sealing ring 662 and a fourth sealing ring 664 may be clamped together and inserted in a slot (not shown) in a bottom section 637 of the extended portion 635 of the fixed arm 124.

When assembled, the elbow joint 128 rotates about the elbow axis 665, the stop screw 640 and the bumper pins 675A and 675B controlling a range of rotational movement of the elbow joint 128. For example, the shaft 634 may move from a first constrained position (where the stop screw 640 makes face contact with the bumper pin 675A) to a second constrained position, where the stop screw 640 makes face contact with the bumper pin 675B. In one example, the shaft 634 may move between the first and second constrained portions, as shown by double direction arrows 677. In this example, the elbow joint 128 may move through an angle (e.g., the angle 624 shown in FIG. 6B) that range from 10 degrees to 190 degrees, where the first constrained position corresponds to the elbow joint at 10 degrees and the second constrained position corresponds to the elbow joint at 190 degrees. In this way, the stop screw 640 and the bumper pins 675A and 675B may be used to constrain movement of the elbow joint 128 within a desired rotational range.

Referring to FIG. 6E, a schematic view 682 of the articulating arm 130 adjusted through a plurality of positions to reorient the display monitor 134, is disclosed. The articulating arm 130 is coupled to the display monitor 134 via the wrist joint 132 on one end, and coupled to the fixed arm 124 via the elbow joint 128 at the other end.

The articulating arm 130 may be adjusted from a first position to a second position while the elbow joint 128 is kept in a fixed position. In this case, the articulating arm 130 may be adjusted through an angle 684 defined between arm axes 686 and 688, thereby moving the display monitor 134 from a first location (where the arm axis 686 is perpendicular to the display monitor 134) to a second location, where the display monitor 134 may be positioned adjacent or above the C-arm 104. As an example, the angle 684 may range from 0 degrees to 45 degrees, when the articulating arm 130 is adjusted between the first and second positions to reorient the display monitor 134 between the first position and second position. In one example, the angle 684 may be 0 degrees when the arm axis 686 is perpendicular to the display monitor 134. Although shown as fixed, the elbow joint 128 may be movable when the articulating arm 130 is adjusted between the first and second positions.

Alternatively, the articulating arm 130 may be adjusted from the first position to a third position while the elbow joint 128 is fixed or movable. In this case, the articulating arm 130 may be adjusted through an angle 686 defined between arm axes 686 and 690, thereby moving the display monitor 134 from the first location to a third location, where the display monitor 134 may be positioned adjacent or below the C-arm 104. As an example, when the articulating arm 130 is adjusted between the first and third positions to reorient the display monitor 134 between the first location and third location, the angle 686 may range from 0 degrees to −45 degrees.

When adjusted from the first location to the second location, the display monitor 134 may move through a vertical distance 694 and a horizontal distance 695. As an example, the vertical distance 694 may range from 0 mm to 179 mm and the horizontal distance 695 may range from 0 mm to 74 mm. In one example, both the vertical distance 694 and horizontal distance 695 may be zero when the display monitor 134 is in a horizontal position, with the articulating arm 130 adjusted perpendicular to the display monitor 134. Alternatively, the display monitor 134 may move through a vertical distance 696 and a horizontal distance 698, when the display monitor 134 is adjusted from the first location to the third location. As an example, the vertical distance 696 may range from 0 mm to 179 mm and the horizontal distance 698 may range from 0 mm to 74 mm. In one example, both the vertical distance 696 and horizontal distance 698 may be zero when the display monitor 134 is in the horizontal position, with the articulating arm 130 adjusted perpendicular to the display monitor 134. In this way, the articulating arm 130 may be adjusted through a plurality of positions (while the elbow joint 128 is fixed or movable) to reorient the display monitor 134 from one location to another location.

Referring to FIGS. 7A-B, a side view 700 and a plan view 702, respectively of the imaging system 100 with the display monitor 134 placed in a retracted position behind the C-arm 104 is disclosed. The display monitor 134 may be moved from the first side 512 of the C-arm 104 to the retracted position behind the C-arm 104 by rotating the articulating arm 130 via the elbow joint 128, and moving the display monitor 134 over the upper half of the C-shaped portion 105 from the first side of the C-arm 104 to the retracted position, without readjusting the position of the fixed arm 124.

The articulating arm 130 may be reoriented by rotating the elbow joint 128 about the elbow rotational axis 168 in such a manner that the display monitor 134 is moved from the first side 512 of the C-arm 104 to the retracted position behind the C-arm 104. In this case, the elbow joint 128 may be adjusted such that the articulating arm 130 is moved from the first side 512 of the C-arm 104 to the retracted position behind the C-arm 104 while the fixed arm 124 is kept in a fixed position, for example, by engaging a brake (not shown) on the shoulder joint to lock the fixed arm 124. When secured in the fixed position, the fixed arm 124 may be positioned at the angle 606 from the central axis 164 of the C-shaped portion 105 of the C-arm 104, as shown in FIG. 7B. Alternatively, the fixed arm 124 may be adjustable and may be moved from one position to another position when the articulating arm 130 is adjusted. After reorienting the elbow joint 128, the position of the articulating arm 130 may be adjusted such that the articulating arm 130 forms the angle 504 between the elbow axis 412 and arm center line 505, as shown in FIG. 7A. Further, the display monitor 134 may be adjusted to face a particular direction by adjusting the wrist joint 132 on one end of the articulating arm 130. When positioned behind the C-arm 104 in the retracted position, the articulating arm 130 and display monitor 134 may be easily moved over the C-arm 104 and towards the second side 514 of the C-arm 104 without moving the display monitor 134 further behind from the C-arm 104. For example, the fixed arm 124 and display monitor 134 never swing behind axis 510 while the display monitor is moving over the C-arm 104 from the first side 512 to the second side 514 of the C-arm.

Referring to FIGS. 8A-D, a first side view 800, a first plan view 802, a second side view 804 and a second plan view 806, respectively of the imaging system 100 with the display monitor 134 positioned behind the C-arm 104 is disclosed. The display monitor 134 may be moved from the retracted position behind the C-arm 104 to a position where the display monitor 134 faces the first side 512 of the C-arm 104 by rotating the fixed arm 124 via the shoulder joint without readjusting the elbow joint 128 and articulating arm 130.

The fixed arm 124 may be adjusted outward and away from the C-arm 104 via the shoulder joint 126 which is rotated about the shoulder axis 408, while the articulating arm 130 coupled to the elbow joint 128 may be maintained in a fixed position, as shown in FIGS. 8A-B. The fixed arm 124 may be positioned at an angle 808 defined between central axis 164 and an arm center line 810, as shown in FIG. 8B. The angle 808 may range from 0 to 120 degrees, when the position of the fixed arm 124 is adjusted to reorient the display monitor 134, for example. The display monitor 134 may be positioned behind the C-arm 104 at a location where the display monitor may be easily adjusted without being obstructed by the upper half of the C-shaped portion 105 of the C-arm 104. For example, when the angle 808 is zero degrees, the center line 810 of the fixed arm 124 is aligned with the central axis 164 along the C-arm 104. In other examples, where the angle 808 is greater than zero degrees, the fixed arm 124 may be positioned in a skew direction from the central axis 164.

The shoulder joint 126 may be rotatable about the shoulder axis 408 such that the display tablet 136 faces a particular direction, as shown in FIG. 8A. In one example, the shoulder joint 126 may be rotated to orient the display tablet 136 through a first angle 812 defined between the central axis 164 and axis 816 on a first side 820 of the cross member 120, and a second angle 814 defined between the central axis 164 and an axis 818 on a second side 822 of the cross member 120, as shown in FIG. 8B. In another example, the first angle 812 may range from 0 to 120 degrees, and the second angle 814 may range from 0 to −120 degrees, where each of the first angle 812 and second angle 814 is equal to zero degrees along the central 164.

The fixed arm 124 may be further adjusted away from the C-arm 104 without readjusting the elbow joint 128 and articulating arm 130, as shown in FIG. 8C-D. For example, the fixed arm 124 may be further adjusted away from the C-arm 104 and towards the second side 514 of the C-arm, such that the angle 808 is in a range of 0-120 degrees. In one example, the angle 808 is equal to zero degrees when the center line 810 of the fixed arm 124 is aligned with the central axis 164 and the elbow joint 128 is directly aligned with the C-arm 104 in a front position. In this case, the display monitor 134 may be placed in a position where the C-arm 104 does not obstruct movement of the articulating arm 130 when the display monitor 134 is reoriented. In this way, the shoulder joint 126 may be rotatable about the shoulder axis 408 to reorient the fixed arm 124 from the first side 512 of the C-arm 104 to the second side 514 of the C-arm 104 while the C-arm 104 remains fixed, the first side 512 arranged opposite the second side 514 relative to a central axis 164 arranged through a center of the C-shaped portion 105.

Referring to FIGS. 9A-B, a side view 900, and plan view 902, respectively of the imaging system 100 with the display monitor 134 facing the second side 514 of the C-arm 104 is disclosed. The display monitor 134 may be moved from behind the C-arm 104 to the second side 514 of the C-arm 104 by rotating the articulating arm 130 via the elbow joint 128 while the fixed arm 124 may be kept in a fixed position, for example by locking brakes (e.g., brake handle 122 shown in FIG. 1) on the shoulder joint 126.

The articulating arm 130 may be adjusted via the elbow joint 128 without readjusting the position of the fixed arm 124, as shown in FIG. 9A-B. The fixed arm 124 may be kept in the fixed position, such that the arm defines the angle 808 between central axis 164 and arm center line 810. The elbow joint 128 may be rotated about the elbow rotational axis 168, from a position where the display monitor 134 faces the upper half of the C-shaped portion 105 of the C-arm 104 to a different position where the display monitor 134 faces away from the C-arm 104 in the second side of the C-arm.

When positioned on the second side 514 of the C-arm 104, the articulating arm 130 and display monitor 134 may be reoriented without the C-arm 104 causing any obstruction. The articulating arm 130 may be extended out past the C-arm 104, and the wrist joint 132 may be adjusted to orient the display monitor 134 in a direction facing the detector 108, as disclosed further below with reference to FIGS. 10A-B. In this way, the fixed arm 124 may be oriented in a position that allows the articulating arm 130 to be rotated via the elbow joint 128 to positions where the C-arm does not obstruct movement of the display monitor 134, when the monitor is moved from the first side 512 to the second side 514 of the C-arm 104.

Referring to FIGS. 10A-B, a side view 1000, and plan view 1002, respectively of the imaging system 100 with the display monitor 134 positioned in the second side 514 of the C-arm 104 is disclosed. The display monitor 134 may be extended forward and past the C-arm 104 to the second side 514 of the C-arm 104 by rotating the fixed arm 124 via the shoulder joint 126, and adjusting the articulating arm 130 via the elbow joint 128.

When the brake (not shown) on the shoulder joint 126 is disengaged, the fixed arm 124 may be moved forward and towards the C-arm 104. The fixed arm 124 may be positioned at the angle 808 formed between the central axis 164 and arm center line 810. In one example, the magnitude of the angle 808 may range from −15 to −45 degrees. In other examples, the magnitude of the angle 808 may range from 0 to −115 degrees. The articulating arm 130 may be adjusted by rotating the elbow joint 128 about the elbow rotational axis 168 in a direction away from the C-arm 104, and extending the articulating arm 130 forward in a horizontal direction, such that the arm makes an angle 1004 between the elbow axis 412 and arm center line 505. Further, the wrist joint 132 may be adjusted to orient the display monitor 134 in a direction of the arrow 608 at the second side 514 of the C-arm 104, as shown in FIG. 10B. When positioned at the second side 514 of the C-arm 104, the display monitor 134 may be at a second distance 1006 from axis 612, adjacent to an operator (not shown) operating the imaging system 100. In one example, the second distance 1006 of the display monitor 134 from the axis 612 may be 337 cm. In another example, the second distance 1006 of the display monitor 134 from the axis 612 may range from 190 mm to 857 mm. In this example, the display monitor 134 may be moved through a plurality of distances that allow different operators to visually inspect images on the display monitor 134 with ease.

In this way the display monitor 134 may be reoriented by rotating the fixed arm 124 inward toward the C-arm 104 via the shoulder joint 126 while rotating the articulating arm 130 further inward and towards the C-arm 104 via the elbow joint 128 to move the display monitor 134 into the extended position on the second side 514 of the C-arm 104.

Turning to FIG. 11, a method 1100 for repositioning the display monitor (such as display monitor 134 shown in FIGS. 4A-10B) coupled to an integrated arm (e.g., integrated arm 115 shown in FIGS. 4A-B) of an imaging system (e.g., system 100 shown in FIGS. 4A-10B) from a first side of a C-arm (e.g., C-arm 104 shown in FIGS. 4A-10B) to a second side of the C-arm is disclosed.

At 1102, the method 1100 includes moving the display monitor from a parked position to an unlocked position behind the C-arm. When the imaging system is placed in the parked position, the monitor may be placed in a pocket (e.g., pocket 404 shown in FIG. 4A). When in the parked position, the display monitor may be positioned behind the C-arm at a height that allows the imaging system to be transported with ease. In this case, the imaging system may be transported from one position to another by rolling the system using the plurality of the wheels coupled to a lower portion of a base unit that supports the C-arm and integrated arm coupled to the display monitor.

When the imaging system is activated, the display monitor may be adjusted from the parked position to the unlocked position by moving the articulating arm upward while the elbow joint and fixed arm remain in fixed positions. The elbow joint couples the articulating arm which is coupled directly to the display monitor, and to a curved portion of the fixed arm, where the fixed arm may couple the articulating arm to the C-arm. When moved from the parked position to the unlocked position behind the C-arm, a height of the display monitor may increase, thereby creating more space for maneuvering the integrated arm and display monitor. A brake on the shoulder joint may be unlocked to allow the fixed arm to move freely. In this case, only a single brake may be provide on the integrated arm to expedite adjusting of the display monitor before or during imaging operations. A wrist joint (e.g., wrist joint 132 shown in FIGS. 5A-B), on one end of the articulating arm coupling the display monitor, may be adjusted to orient the display monitor in a particular direction within the horizontal plane.

At 1104, the display monitor may be moved from the unlocked position behind the C-arm to the first side of the C-arm. The display monitor may be moved from behind the C-arm to the first side of the C-arm by rotating the fixed arm via the shoulder joint, and adjusting the articulating arm via the elbow joint. As an example, the fixed arm may be moved from a position where a straight portion (e.g., portion 125 shown in FIG. 5B) of the arm lies along a central axis (e.g., axis 164 shown in FIG. 5B) of the C-arm, to a position where the fixed arm lies along an arm center line that defines an angle (e.g., angle 606 shown in FIG. 6B) with the central axis of the C-arm.

The shoulder joint may include a brake adapted to lock rotation of the shoulder joint. In this way, the fixed arm may be locked into a fixed position while allowing the articulating arm to rotate via the elbow joint. As an example, the elbow joint may be rotated from a first position where the elbow joint faces away from the C-arm to a second position where the elbow joint faces an upper half of the C-shaped portion of the C-arm. Subsequently, the articulating arm may be rotated (via the elbow joint) to face the upper half of the C-shaped portion of the C-arm, and extended forward and toward the first side of the C-arm. In this way the display monitor may be reoriented by rotating the fixed arm inward toward the C-arm via the shoulder joint while rotating the articulating arm further inward and towards the C-arm via the elbow joint to move the display monitor into an extended position on the first side of the C-arm. The articulating arm may be adapted to pivot at the elbow joint, while the wrist joint on one end of the articulating arm may be adjusted such that the display monitor faces a direction of an operator using the imaging system. When positioned at the first side of the C-arm, the display monitor may be positioned at a threshold distance that allows the operator the ability to visually inspect images on the display monitor with ease.

At 1106, the method 1100 may include rotating the display monitor from the extended position on the first side of the C-arm, over the C-arm and towards a retracted position behind the C-arm via the elbow joint. By rotating the articulating arm across a top half of a C-shaped portion of the C-arm, the display monitor may be moved from the first side of the C-arm to towards the retracted position with less difficulty. In this case, the fixed arm may remain in a fixed position when the display monitor is moved from the first side of the C-arm to the retracted position.

At 1108, the method 1100 may include adjusting both the shoulder joint and elbow joint to move the display monitor from the retracted position into an extended position on the second side of the C-arm. In this case, the extended position on the second side of the C-arm may include the display monitor being positioned away from a base unit (e.g., base unit 102 shown in FIGS. 10A-B) of the imaging system. The fixed arm may be extended to the second side of the C-arm via the shoulder joint that couples a straight portion of the fixed arm to the C-arm. The straight portion also couples to the curved portion of the fixed arm. The display monitor may be moved from the first side of the C-arm to the second side of the C-arm by moving the monitor over the top half of the C-shaped portion of the C-arm without swinging the monitor around a back side of the base unit coupled to the C-arm. In this way, the display monitor may be expeditiously reoriented from one position to another using the integrated arm comprising the fixed arm coupled to the shoulder joint, and the articulating arm coupled on one end to the fixed arm via the elbow joint, and coupled at another end to the display monitor via the wrist joint. The method then exits.

FIGS. 1-10B show example configurations with relative positioning of the various components of the imaging system. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

The technical effect of the disclosure may include improved mobility of the integrated arm coupled to the display monitor of the imaging system, where the display monitor may be easily moved from a first position to a second position without causing undue difficulty to an operator of the imaging system. Adjusting the display monitor from the first position to the second position involves moving the monitor over the top of the C-arm (instead of via the back end of the C-arm) to expedite the adjusting of the display monitor during imaging operations. Further, the integrated arm of the imaging system may include only a single brake on the shoulder joint (instead of a plurality of brakes), thereby allowing the integrated arm to be quickly adjusted to reorient the display monitor without requiring undue effort from the operator. Another technical effect of the disclosure may include improved flexibility of the integrated arm where a height of the display monitor and a distance of the monitor from the operator may be adjustable to suit needs of different operators and various imaging procedures. Yet another technical effect of the disclosure may include improved flexibility of the C-arm during imaging operations. For example, the C-arm may be adjustable via the rotational joint that couples C-arm to the base unit. In this case, the x-ray source and detector coupled on opposite sides of the C-arm may be adjusted through a plurality of positions to capture multiple images of a patient's body without moving or repositioning the patient. A further technical effect of the disclosure may include improved operation of the imaging system, since a single brake may be provided on the integrated arm, thereby allowing the display monitor to be reoriented expeditiously without spending time unlocking and locking different brake systems.

In one embodiment, an imaging system may comprise: a base unit; a C-arm coupled to the base unit and including an x-ray source and detector positioned on opposite ends of a C-shaped portion of the C-arm; and a display monitor attached to the C-arm via an integrated arm, wherein the display monitor is movable between a first position on a first side of the C-arm, to a second position on a second side of the C-arm by traveling over a top of an upper half of the C-shaped portion.

In a preceding example, the integrated arm includes three movable joints offset from one another along the integrated arm. In any or all of the preceding examples, additionally or optionally, the integrated arm includes a fixed arm and an articulating arm coupled to one another via an elbow joint. In any or all of the preceding examples, additionally or optionally, the fixed arm includes two offset joints, including the elbow joint and a shoulder joint, arranged on opposite ends of the fixed arm, wherein the shoulder joint of the two offset joints couples a straight portion of the fixed arm to the C-arm and the elbow joint of the two offset joints couples a curved portion of the fixed arm to the articulating arm. In any or all of the preceding examples, additionally or optionally, the curved portion of the fixed arm follows a radius of curvature of a top half of the C-shaped portion of the C-arm and wherein when the display monitor and integrated arm are in a parked position, the curved portion of the fixed arm curves along a portion of, but offset from, the top half of the C-shaped portion of the C-arm.

In any or all of the preceding examples, additionally or optionally, the shoulder joint is rotatable in a horizontal plane and is adapted to rotate the fixed arm from the first side of the C-arm to the second side of the C-arm while the C-arm remains fixed, the first side arranged opposite the second side relative to a central axis arranged through a center of the C-shaped portion. Any or all of the preceding examples may further comprise, a single brake coupled to the shoulder joint and adapted to lock rotation of the shoulder joint and wherein the elbow joint does not include a brake. In any or all of the preceding examples, additionally or optionally, the articulating arm is adapted to pivot at the elbow joint and wherein the articulating arm is coupled to the display monitor via a wrist joint In any or all of the preceding examples, additionally or optionally, the elbow joint is rotatable in a horizontal plane and is adapted to rotate the articulating arm relative to the fixed arm. In any or all of the preceding examples, additionally or optionally, the C-arm includes an extended portion coupled to the base unit, wherein the C-shaped portion is adapted to rotate at least 180 degrees in each direction via a rotatable joint coupling the C-shaped portion to the extended portion of the C-arm, and wherein the integrated arm is coupled to the extended portion of the C-arm. Any or all of the preceding examples may further comprise, a pocket adapted to receive the display monitor when the imaging system is placed in a parked position. Any or all of the preceding examples may further comprise, a display tablet coupled to vertical member attached to the shoulder joint. In any or all of the preceding examples, additionally or optionally, the base unit is movable via a plurality of wheels coupled to a bottom of the base unit.

Another embodiment may include a method for repositioning a display monitor coupled to a C-arm of an imaging system via an integrated arm, comprising: rotating the display monitor from an extended position on a first side of the C-arm to a retracted position behind the C-arm via an elbow joint coupling an articulating arm of the integrated arm, the articulating arm coupled directly to the display monitor, to a curved portion of a fixed arm of the integrated arm, the fixed arm coupling the articulating arm to the C-arm; rotating the articulating arm across a top half of a C-shaped portion of the C-arm and to a second side of the C-arm via a shoulder joint coupling a straight portion of the fixed arm to the C-arm, the straight portion coupled to the curved portion; and adjusting both the elbow joint and shoulder joint to move the display monitor into an extended position on the second side of the C-arm, wherein the extended position on each of the first side and the second side include the display monitor being positioned away from a base unit of the imaging system.

In the preceding example, additionally or optionally, adjusting both the elbow joint and shoulder joint includes: rotating the articulating arm outward and away from the C-arm via the elbow joint; and rotating the fixed arm inward toward the C-arm via the shoulder joint while rotating the articulating arm further outward and away from the C-arm via the elbow joint to move the display monitor into the extended position on the second side of the C-arm. Any or all of the preceding examples, may further comprise: rotating the C-shaped portion of the C-arm about a rotating joint coupled to an extended portion of the C-arm, the extended portion coupled to each of the base unit and the fixed arm, to switch a position of an x-ray source relative to a detector, the x-ray source coupled to a first end of the C-shaped portion and the detector coupled to a second end of the C-shaped portion. In any or all of the preceding examples, additionally or optionally, rotating the articulating arm across the top half of the C-shaped portion of the C-arm and to the second side of the C-arm includes moving the display monitor over the top half of the C-shaped portion without swinging the display monitor around a back side of the base unit, the C-arm coupled to the base unit.

In yet another embodiment, an imaging system may comprise: a base unit; a C-arm coupled to the base unit at an extended portion of the C-arm and including an x-ray source and detector positioned on opposite ends of a C-shaped portion of the C-arm; a fixed arm coupled directly to the extended portion of the C-arm and including two joints offset from one another, where a first joint of the two joints is arranged at the extended portion of the C-arm; an articulating arm coupled to the fixed arm at a second joint of the two joints of the integrated arm; and a display monitor coupled to an end of the articulating arm via a third joint.

In any or all of the preceding examples, additionally or optionally, the C-shaped portion of the C-arm is rotatable about a rotating joint coupling the C-shaped portion to the extended portion of the C-arm and wherein the C-shaped portion is rotatable, via the rotating joint, into a first position where the x-ray source is positioned vertically above the detector and a second position where the detector is positioned vertically above the x-ray source. In any or all of the preceding examples, additionally or optionally, the fixed arm includes a straight portion and a curved portion, the straight portion coupled directly to the extended portion of the C-arm and extending toward the C-shaped portion of the C-arm and the curved portion coupled to the articulating arm and having a curved shape that curves over and along a portion of a top half of the C-shaped portion.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. An imaging system, comprising:
a base unit;
a C-arm coupled to the base unit and including an x-ray tube and a detector positioned on opposite ends of a C-shaped portion of the C-arm; and
a display monitor attached to the C-arm via an integrated arm comprising a fixed arm and an articulating arm coupled to one another via an elbow joint, wherein the display monitor is movable between a first position on a first side of the C-arm, to a second position on a second side of the C-arm by traveling over a top of an upper half of the C-shaped portion via a shoulder joint coupled to the fixed arm at an end opposite the elbow joint.

2. The imaging system of claim 1, wherein the integrated arm includes three movable joints offset from one another along the integrated arm.

3. The imaging system of claim 1, wherein the elbow joint and the shoulder joint are offset to each other, and wherein the shoulder joint couples a straight portion of the fixed arm to the C-arm and the elbow joint couples a curved portion of the fixed arm to the articulating arm.

4. The imaging system of claim 3, wherein the curved portion of the fixed arm follows a radius of curvature of a top half of the C-shaped portion of the C-arm and wherein when the display monitor and the integrated arm are in a parked position, the curved portion of the fixed arm curves along a portion of, but offset from, the top half of the C-shaped portion of the C-arm.

5. The imaging system of claim 3, wherein the shoulder joint is rotatable in a horizontal plane and is adapted to rotate the fixed arm from the first side of the C-arm to the second side of the C-arm while the C-arm remains fixed, the first side arranged opposite the second side relative to a central axis arranged vertically through a center of the C-shaped portion.

6. The imaging system of claim 5, further comprising a single brake coupled to the shoulder joint and adapted to lock rotation of the shoulder joint and wherein the elbow joint does not include a brake.

7. The imaging system of claim 1, wherein the elbow joint is rotatable in a horizontal plane and is adapted to rotate the articulating arm relative to the fixed arm.

8. The imaging system of claim 1, wherein the articulating arm is adapted to pivot at the elbow joint and wherein the articulating arm is coupled to the display monitor via a wrist joint.

9. The imaging system of claim 1, wherein the C-arm includes an extended portion coupled to the base unit, wherein the C-shaped portion is adapted to rotate at least 180 degrees in each direction via a rotatable joint coupling the C-shaped portion to the extended portion of the C-arm, and wherein the integrated arm is coupled to the extended portion of the C-arm.

10. The imaging system of claim 1, further comprising a pocket adapted to receive the display monitor when the imaging system is placed in a parked position.

11. The imaging system of claim 1, further comprising a display tablet coupled to a vertical member attached to the shoulder joint.

12. The imaging system of claim 1, wherein the base unit is movable via a plurality of wheels coupled to a bottom of the base unit.

13. A method for repositioning a display monitor coupled to a C-arm of an imaging system via an integrated arm, comprising:
rotating the display monitor from an extended position on a first side of the C-arm to a retracted position behind the C-arm via an elbow joint coupling an articulating arm of the integrated arm, the articulating arm coupled directly to the display monitor, to a curved portion of a fixed arm of the integrated arm, the fixed arm coupling the articulating arm to the C-arm;
rotating the articulating arm across a top half of a C-shaped portion of the C-arm and to a second side of the C-arm via a shoulder joint coupling a straight portion of the fixed arm directly to the C-arm, the straight portion coupled to the curved portion; and
adjusting both the elbow joint and the shoulder joint to move the display monitor into an extended position on the second side of the C-arm, wherein the extended position on each of the first side and the second side includes the display monitor being positioned away from a base unit of the imaging system.

14. The method of claim 13, wherein adjusting both the elbow joint and the shoulder joint includes:
rotating the articulating arm outward and away from the C-arm via the elbow joint; and
rotating the fixed arm inward toward the C-arm via the shoulder joint while rotating the articulating arm further outward and away from the C-arm via the elbow joint to move the display monitor into the extended position on the second side of the C-arm.

15. The method of claim 13, further comprising rotating the C-shaped portion of the C-arm about a rotating joint coupled to an extended portion of the C-arm, the extended portion coupled to each of the base unit and the fixed arm, to switch a position of an x-ray source relative to a detector, the x-ray source coupled to a first end of the C-shaped portion and the detector coupled to a second end of the C-shaped portion.

16. The method of claim 13, wherein rotating the articulating arm across the top half of the C-shaped portion of the C-arm and to the second side of the C-arm includes moving the display monitor over the top half of the C-shaped portion without swinging the display monitor around a back side of the base unit, the C-arm coupled to the base unit.

17. An imaging system, comprising:
- a base unit;
- a C-arm coupled to the base unit at an extended portion of the C-arm and including an x-ray source and a detector positioned on opposite ends of a C-shaped portion of the C-arm;
- a fixed arm coupled directly to the extended portion of the C-arm and including two joints offset from one another and arranged at opposite ends of the fixed arm, where a first joint of the two joints is arranged at the extended portion of the C-arm;
- an articulating arm coupled to the fixed arm at a second joint of the two joints of the integrated arm; and a display monitor coupled to an end of the articulating arm via a third joint.

18. The imaging system of claim 17, wherein the C-shaped portion of the C-arm is rotatable about a rotating joint coupling the C-shaped portion to the extended portion of the C-arm and wherein the C-shaped portion is rotatable, via the rotating joint, into a first position where the x-ray source is positioned vertically above the detector and a second position where the detector is positioned vertically above the x-ray source.

19. The imaging system of claim 17, wherein the fixed arm includes a straight portion and a curved portion, the straight portion coupled directly to the extended portion of the C-arm and extending toward the C-shaped portion of the C-arm and the curved portion coupled to the articulating arm and having a curved shape that curves over and along a portion of a top half of the C-shaped portion.

* * * * *